US007910328B2

(12) United States Patent
Shimizu et al.

(10) Patent No.: US 7,910,328 B2
(45) Date of Patent: Mar. 22, 2011

(54) PROMOTER OF NOVEL CALCIUM-INDEPENDENT PHOSPHOLIPASE A2

(75) Inventors: Takao Shimizu, Tokyo (JP); Koji Kishimoto, Tokyo (JP); Yasuyoshi Watanabe, Osaka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 91 days.

(21) Appl. No.: 11/984,901

(22) Filed: Nov. 26, 2007

(65) Prior Publication Data

US 2008/0154028 A1 Jun. 26, 2008

Related U.S. Application Data

(62) Division of application No. 10/468,519, filed as application No. PCT/JP01/06071 on Jul. 13, 2001, now Pat. No. 7,332,318.

(30) Foreign Application Priority Data

Feb. 22, 2001 (JP) ................................ 2001-045938

(51) Int. Cl.
*C12P 21/06* (2006.01)
*C12N 15/00* (2006.01)
*C12N 5/00* (2006.01)
*C07H 21/02* (2006.01)
*C07H 21/04* (2006.01)
*C07K 14/00* (2006.01)

(52) U.S. Cl. .................... 435/69.1; 435/320.1; 435/325; 435/375; 435/455; 536/23.1; 536/24.1; 536/24.2; 530/350

(58) Field of Classification Search ........................ None
See application file for complete search history.

(56) References Cited

U.S. PATENT DOCUMENTS

| 5,527,698 | A | 6/1996 | Knopf et al. |
| 5,589,170 | A | 12/1996 | Jones et al. |
| 6,801,860 | B1 | 10/2004 | Dessen et al. |

FOREIGN PATENT DOCUMENTS

| EP | 459643 A1 | 12/1991 |
| JP | 11-269198 A1 | 10/1999 |
| WO | WO-96/40721 A1 | 12/1996 |

OTHER PUBLICATIONS

Bonventre et al. Nature 390:622-625; 1997.*
Uozumi et al. Nature 390:618-622; 1997.*
Six et al. BBA 1488:1-19; 2000.*
Dolan-O'Keefe et al. Am. J. Lung Cell Mol. Physiol. 278:L649-L657; 2000.*
Carpten et al. Genomics 64:1-14, 2000.*
Clark et al., "A Novel Arachidonic Acid-Selective Cytosolic PLA2 Contains a Ca2+-Dependent Translocation Domain with Homology to PKC and GAP", Cell, Jun. 14, 1991, 1043-1051, vol. 65 (full version).
International Search Report (English Translation) dated Nov. 6, 2001.
Ichiro Kudou et al., Tanpaku-shitsu, Kakusan, Kouso, vol. 44 , No. 8, pp. 1013-1024. (1999).
Gael Y. et al., "Genes Encoding Multiple Forms of Phospholipase A2 are Expressed in Rat Brain," Neuroscience Letters, vol. 258 pp. 139-413 (1998).
Brian M. Ross et al., "Differential Alteration of Phospholipase A2 Activities in Brain of Patients with Schizophrenia," Brain Research, vol. 821, pp. 407-413 (1999).
James D. Clark et al., "A Novel Arachidonic Acid-selective Cytosolic Phospholipase PLA2 Contains a Ca2+-dependent Translocation Domain with Homology to PKC and GAP," Cell, vol. 65, No. 6, pp. 1043-1051 (1991).
Y. Owada et al., "Molecular Cloning of Rat cDNA for Cytosolic PhospholipaseA2 and the Increased Gene Expression in the Dentate Gyrus Following Transient Forebrain Inshemia," Molecular Brain Research, vol. 27, No. 2, p. 335, (1995).
John D. Sharp et al., "Molecular Cloning and Expression of Human Ca2+-sensitive Cytosolic PhospholipaseA2," Journal of Biological Chemistry, vol. 266, No. 23, pp. 14850-14853 (1991).
Tommasi S., et al. "In Vivo Structure of Two Divergent Promoters at the Human PCNA Locus, Synthesis of Antisense RNA and S Phase-dependent binding of E2F Complexes in Intron 1," Journal of Biological Chemistry, vol. 274, No. 39, pp. 27829-27838, (1999).
Marcheselli VL, et al., "Sustained Induction of Prostaglandin Endoperoxide Syntase-2 by Seizures in Hippocampus, Inhibition by a Platelet-activating Factor Antagonist," Journal of Biological Chemistry, vol. 271, No. 40, pp. 24794-24799 (1996). Bing G. et al., "A Single Dose of Kainic Acid Elevates the Levels of Enkephalins and Activator Protein-1 Transcription Factors in the Hippocampus for up to 1 Year," Proceedings of the National Academy of Sciences, vol. 94, No. 17, p. 9422-9427 (1997).

(Continued)

*Primary Examiner* — Sumesh Kaushal
(74) *Attorney, Agent, or Firm* — Westerman, Hattori, Daniels & Adrian, LLP

(57) ABSTRACT

Novel calcium-independent phospholipases $A_2$; genes encoding the same; an antibody against them; an inherent promoter or a regulator gene which comprises a base sequence occurring in intron and inducing site-specific expression in response to an external stimulus; a method of expressing a target protein in response to an external stimulus; and an organism having this gene transferred thereinto. Novel calcium-independent phospholipases $A_2$ having an amino acid sequence represented by SEQ ID NO: 1, 3 or 5 or an amino acid sequence derived from such an amino acid sequence by the substitution, deletion or addition of one or more amino acids; a gene having a base sequence occurring in an intron and being capable of initiating RNA transcription due to an external stimulus such as a stimulus with kainic acid or an electrical stimulus; a method of regulating expression by using the gene; and an organism having the gene transferred thereinto.

14 Claims, 15 Drawing Sheets

OTHER PUBLICATIONS

Matsuo et al., "Characterization of the Genomic Structure and Promoter of the Mouse NAD+-dependent 15-hydroxyprostaglandin Dehydrogenase Gene," Biochemical Biophysics Research Community, vol. 235, No. 3, pp. 582-586 (1997).

Sequence Search & Alignment pp. 1-2; 2006.

Larsson et al. J. Biol. Chem. 273: 207-214, 1998.

Bowie, et al. Science, 247: 1306-10, 1990.

* cited by examiner

FIG.3

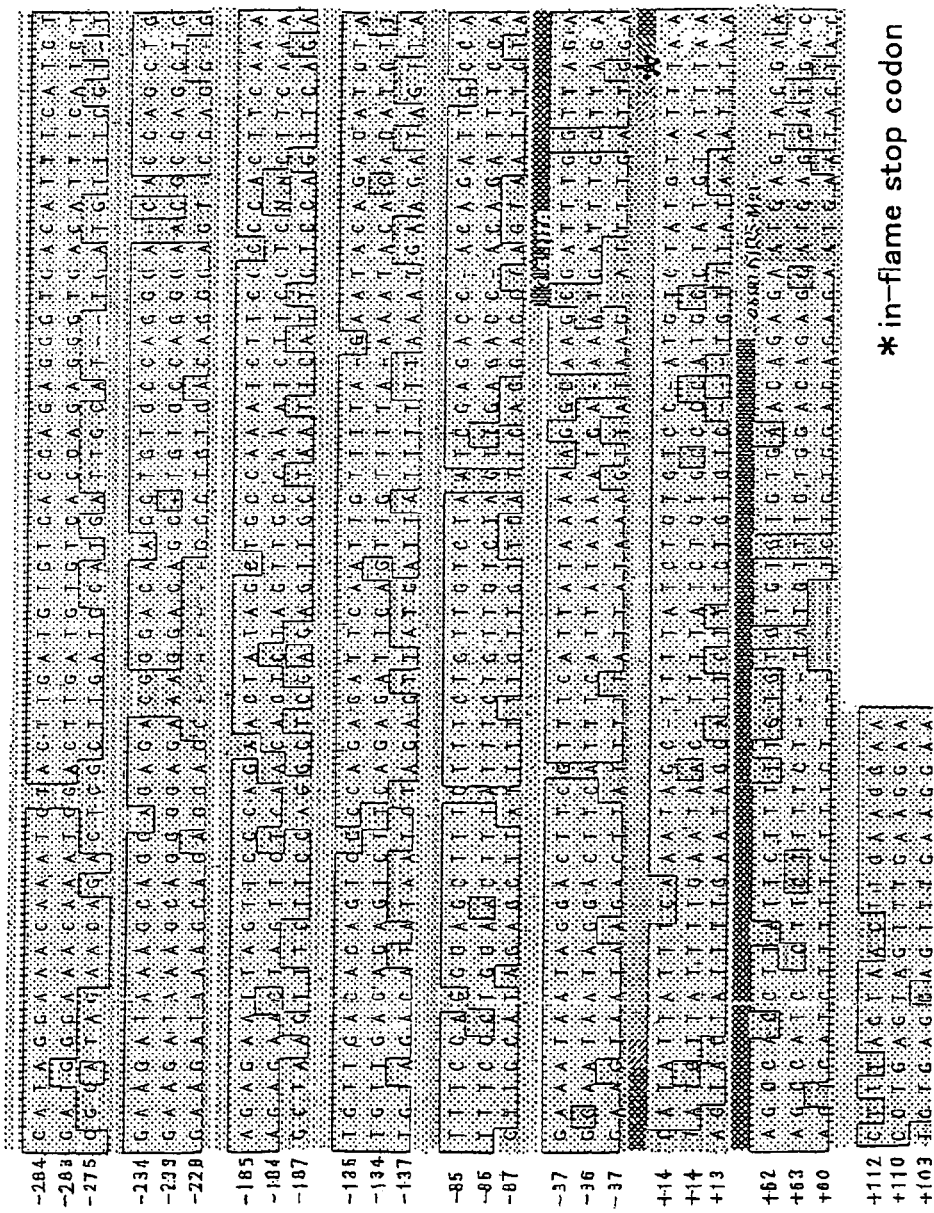
FIG.12 (CONTINUATION)
* in-flame stop codon

US 7,910,328 B2

PROMOTER OF NOVEL CALCIUM-INDEPENDENT PHOSPHOLIPASE A2

CROSS REFERENCE TO RELATED APPLICATIONS

The present application is a Divisional Application of patent application Ser. No. 10/468,519, filed Aug. 19, 2003, which is an application under 35 U.S.C. §371 of PCT/JP2001/06071 filed on Jul. 13, 2001, 2003, now U.S. Pat. No. 7,332,318 which claims the benefit of foreign priority patent application No. 2001-045938 filed Feb. 22, 2001 in Japan. The entire contents of the applications above are incorporated herein by reference.

TECHNICAL FIELD

The present invention relates to a calcium-independent novel phospholipase A2 (having a phospholipase A1 activity as well) and, more particularly, it relates to a novel phospholipase A2 which is a calcium-independent phospholipase A2, is a phospholipase A2 expressed specifically in hippocampus by an external stimulation such as stimulation by kainic acid or electric stimulation and has an amino acid sequence described in SEQ ID NO: 1, NO: 5 or NO: 8 of the Sequence Listing or an amino acid sequence where one or more amino acid(s) in the amino acid sequence is/are substituted with other amino acid(s) or deficient or one or more amino acid(s) is/are added thereto.

The present further relates to gene having a base sequence existing in intron where the base sequence is able to make the initiation of transcription of RNA specifically to hippocampal dentate gyrus by external stimulation such as kainic acid stimulation or electric stimulation possible, to a method for regulating the expression using the same and to a living thing into which the same is introduced.

BACKGROUND OF THE INVENTION

In the gene of eukaryotes, there are many cases where genetic information stipulating the amino acid sequence of protein is interrupted. A moiety having the genetic information of amino acid sequence of protein is called exon while a moiety having no genetic information of amino acid sequence is called intron. After an mRNA precursor is formed by a transcription of genetic DNA, it is subjected to a splicing so that an intron moiety is cut off whereby mature mRNA is resulted.

It has not been clarified yet why such an intron moiety is present in eukaryotes. However, it has been presumed that, in many cases, one exon is coded as a specific domain (functioning region) of protein and, when new protein having the same function is needed during the process of development, necessary protein is able to be produced by a combination of different exons.

With regard to a splicing of the mRNA precursor before being subjected to the splicing, there has been also known the case where not only intron is cut off but also exon moiety is cut off to give mRNA coding for different protein having the function of the same type.

For example, calcitonin gene has six exons—A, B, C, D, calcitonin CCP and CGRP (calcitonin gene related peptide). Exon A and exon B are non-translated region while translated region is other four exons. When a transcription is carried out in nucleus of cell, all exons are included but a process of the splicing varies depending upon organs. For example, in thyroid C cells, exon of the sixth CGRP is also spliced and, as a result, protein of the translated product becomes a peptide comprising C-D-calcitonin CCP mainly exhibiting an action of reducing a serum Ca. In hypothalamic cells, exon of the fifth calcitonin CCP is also spliced and, as a result, protein of the translated product becomes a peptide comprising C-D-CGRP mainly playing a role of regulation of pain and autonomous activity.

When an exon moiety is divided into some as such, it is possible to produce different proteins where several exons are bonded if necessary. Although it has been explained to divide an exon for such a purpose, there has been almost no clarification yet for the necessity of intron except the preparation of an exon moiety. It has been known that many of introns have sequences of 5'-GT and AG-3' at the terminals and that there is an intermediate region abundant in pyrimidine and it has been believed that a splicing is carried out by recognizing those sequences at both terminals.

Phospholipase A2 is widely distributed in mammals and microbes and it is mostly a membrane-bound enzyme and participates in metabolism of membrane phospholipids. A cytosolic phospholipase A2 (cPLA2α) of 85 kDa is a kind of phospholipase A2 and cuts out arachidonic acid mostly from membrane phospholipids producing physiologically active substances by arachidonic acid cascades such as prostaglandin, thromboxane, leukotriene, etc. derived from arachidonic acid. It has been also known that the liberated arachidonic acid participates in various nervous functions in the brain and, until now, the present inventors have shown by a northern blot technique and an in situ hybridization that cPLA2α is abundantly expressed in cranial nerve cells.

On the other hand, kainic acid is a kind of amino acid and has been isolated as an anthelmintic component in *Digenea simplex*. Since kainic acid has a chemical structure similar to glutamic acid, it has been known as a substance binding to a glutamic acid receptor in the brain and the nerve cells of animals resulting in a neuron exciting action.

In order to check the function of phospholipase A2 in the brain, the present inventors have applied kainic acid stimulation or electric stimulation thereto and found a novel phospholipase A2 (455 amino acids; molecular weight: about 50 K) which transiently expresses being limited to dentate gyrus of hippocampus. This enzyme is a partial protein initiating from the 308th methionine of a cytosolic phospholipase A2α (85 K) and, since it also expresses in genetically defective mouse of the said enzyme, it contains a specific promoter which site-specifically expresses in response to stimulation. Although this enzyme is not present under a non-stimulated state, it is expressed by electric stimulation and kainic acid stimulation and, unlike the conventional phospholipase A2, it is independent upon calcium unlike the conventional phospholipase A2, produces eicosanoid, regulates a cerebral function and participates in denaturation, apoptosis and regeneration of nerve cells whereby it is believed to be a molecule holding the key to those cerebral functions.

Further, this novel phospholipase A2 (455 amino acids; molecular weight: about 50 K) is a partial protein initiating from the 308th methionine of a known cytosolic phospholipase A2α (85 K), a promoter region specific for expressing this protein is present in the intron moiety immediately before that and the present inventors have found that, in the intron, there is an intron having a function of making the initiation of transcription of RNA possible. Under a usual state, this intron has no function of initiating the transcription of RNA. However, when a certain condition is set, it has a function of initiating the transcription of RNA not from the inherent transcription position but from the moiety of the base sequence of this intron.

DISCLOSURE OF THE INVENTION

The present invention provides a calcium-independent novel phospholipase A2 (455 amino acids; molecular weight: about 50 K), gene coding therefor and antibody against that.

The present invention further provides an intrinsic promoter or regulatory gene comprising a base sequence existing in intron and site-specifically expressing in response to external stimulation. The present invention furthermore provides a method for expressing a desired protein in response to an external stimulation and to a living thing into which that is introduced.

The present invention still further provides a method for specifically investigating the nerve stem cells since the KIDS cPLA2 of the present invention is specifically expressed in nerve stem cells.

BRIEF DESCRIPTION OF THE DRAWINGS

FIG. 3 is a picture (as a substitute for a drawing) showing the result of an in situ hybridization in the brain of rat. The left side of FIG. 3 is the result of a cross section of the brain while the right side thereof is that from a vertical section of the brain. In FIG. 3, the parts which are in black are colored parts.

In FIG. 6, the lane 1 is the case of a control vector, the lane 2 is the case of cPLA2α/pTracerEF and the lane 3 is the case of KIDS cPLA2/pTracerEF. In FIG. 6, the left side is the case where an anti-V5 epitope IgG was used, the middle is the case where an anti-cPLA2α IgY was used and the right side is the case where an anti-KIDS cPLA2 IgY was used.

In FIG. 7, the left side is that for KIDS cPLA2 of the present invention while the right side is that for cPLA2α. There were used 1-Pam-2-[$^{14}$Cys]arachidonoyl-PC (black dots (●)), 1-Pam-2-[$^{14}$Cys]linoleoyl-PC (black triangles (▲)), 1-Pam-2-[$^{14}$Cys]oleoyl-PC (black squares (■)) and 1-Pam-2-[$^{14}$Cys]palmitoyl-PC (asterisks (*)) as the substrates.

In FIG. 10, the upper column is that for (+/+) of a knockout mouse while the lower column is that for (−/−) of a knockout mouse. In FIG. 10, the left side is that where no kainic acid treatment was carried out (KA (−)) while the right side is that after 3 hours from the kainic acid treatment (KA (+)).

In FIG. 11, the upper column schematically shows exon and intron of cPLA2 in genomic gene.

In FIG. 13, the upper column is nestin as a control, the middle column is the case where nerve stem cells were used and the lower column is the case where mature cells of nerve were used. Pictures on the left side (A) show the positions of each of the cells, pictures on the middle (B) are coloration showing the expression of KIDS cPLA 2 of the present invention and pictures at the right side are those where A at the left side and B at the middle were piled to confirm the positions in both.

In FIG. 14, the probe used is P90-P27 of 252 bp in the upper column, P19-P27 of 290 bp in the second column and G3 PDH and nestin in the lower two columns as controls. The lowermost picture of FIG. 14 shows the initiation positions for transcription of KIDS cPLA 2 at the 5'-side and sequential positions of the probes used in the upper two columns in FIG. 14. The lanes in FIG. 14 are control and stimulations by kainic acid (KA (10 μM)), by kainic acid and CNQX (KA (10 μM)+CNQX (20 μM)) and by glutamic acid (Glu (50 μM)) from the left side.

BEST MODE FOR CARRYING OUT THE INVENTION

Figure 1:
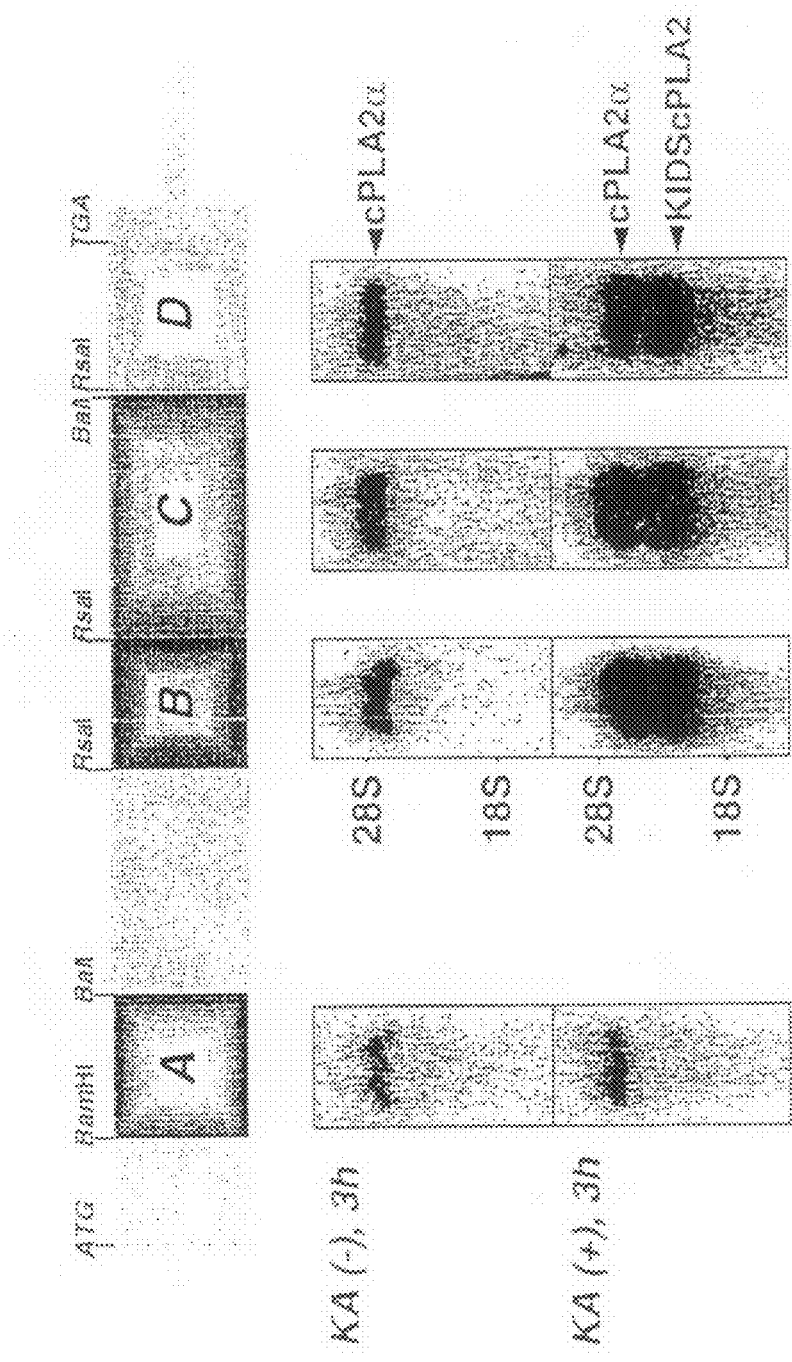
FIG. 1 is a picture (as a substitute for a drawing) showing the result of a northern blotting using various sites of cPLA2 as probes. The upper column of FIG. 1 shows a base sequence of cPLA2. A, B, C and D show the probes. The middle column of FIG. 1 is the case where no kainic acid treatment is carried out (KA(−)) and the lower column of FIG. 1 is the case of after 3 hours from the kainic acid treatment (KA(+), 3 h).

The present invention relates to a calcium-independent novel phospholipase A2 and, more particularly, it relates to a calcium-independent and hippocampus-specific phospholipase A2 which is a phospholipase A2 having an amino acid sequence described in SEQ ID NO: 1, NO: 5 or NO: 8 of the Sequence Listing or an amino acid sequence where one or more amino acid(s) in the amino acid sequence is/are substituted with other amino acid(s) or deficient or one or more amino acid(s) is/are added thereto, to gene coding therefor and an antibody where full length or fragment thereof is an antigen.

The present further relates to gene having a base sequence existing in intron where the base sequence is able to make the initiation of transcription of RNA by external stimulation such as kainic acid stimulation or electric stimulation possible and, more particularly, it relates to gene which is able to make the initiation of transcription of RNA possible in a site-specific manner. Preferred examples of the gene of the present invention are genes having the base sequence described in SEQ ID NO: 12, NO: 13 or NO: 14 of the Sequence Listing and having the base sequence comprising a partial sequence where a part thereof is deleted, added or substituted.

The present invention further relates to a promoter having a base sequence existing in intron and being able to make the initiation of transcription of RNA by external stimulation such as kainic acid stimulation or electric stimulation possible and, more particularly, it relates to the above-mentioned promoter where the initiation of transcription of RNA is in a site-specific manner and to a regulatory gene having a regulatory element at the upper stream of the said promoter.

The present invention furthermore relates to a process wherein any of the above-mentioned gene, the above-mentioned promoter or the above-mentioned regulatory gene is introduced into the upper stream of the gene coding for protein to initiate the transcription of RNA by external stimulation such as kainic acid stimulation or electric stimulation preferably in a site-specific manner whereby the said protein is expressed in response to the external stimulation and to a living thing wherein any of the above-mentioned gene, the above-mentioned promoter and the above-mentioned regulatory gene is introduced into the upper stream of the gene coding for protein.

The present invention still further relates to a method for a specific investigation of nerve stem cells by expression of KIDS cPLA 2 of the present invention. Thus, the present invention relates to a method for the detection or the identification of nerve stem cells by detecting or identifying the mRNA coding for a calcium-independent and novel phospholipase A2 (to be more specific, a phospholipase A2 which is calcium-independent and hippocampus-specific and has an amino acid sequence described in SEQ ID NO: 1, NO: 5 or NO: 8 of the Sequence Listing or an amino acid sequence where one or more amino acid(s) is/are substituted with other amino acid or deleted or one or more amino acid(s) is/are added) by stimulating the nerve cells by external stimulation.

During a course of the study for investigating the function of phospholipase A2 in the brain, the present inventors prepared slices of the brain of rat into which kainic acid was intraperitoneally injected and histochemically checked the expression of mRNA using cPLA2 as a probe (searching element). For the selection of a probe, confirmation was carried out by means of a northern blotting usually using different sites of the cPLA2 whereupon it was found that, when a specific site (5'-terminal) was used, mRNA having a shorter length (about 1.8 kilo base pairs) than cPLA2 was induced.

Result of the northern blotting is shown in FIG. 1 as a picture which is a substitute for a drawing. The upper column of FIG. 1 shows a base sequence of cPLA2. The left end is a translation initiation codon (ATG) and the parts used as a probe are shown by A, B, C and D. Thus, probe A is a part from BamHI to BalI, probe B is a part from RsaI to RsaIBalI, probe C is a part from RsaI to BalI and probe D is a part from RsaI to termination codon (TGA).

The middle column of FIG. 1 is the case where no kainic acid treatment was carried out (KA(−)). The lower column of FIG. 1 is the case after 3 hours from the kainic acid treatment (KA(+), 3 h). When no kainic acid treatment was carried out (KA(−)) (the middle column of FIG. 1), a plot was noted at the position of cPLA2α only while, in the case of 3 hours after a kainic acid treatment when that treatment was carried out (KA(+)), plots of shorter chain length were able to be observed in probes B, C and D at the 5'-terminal side not only at the position of cPLA2α but also at the position beneath that.

Figure 2:
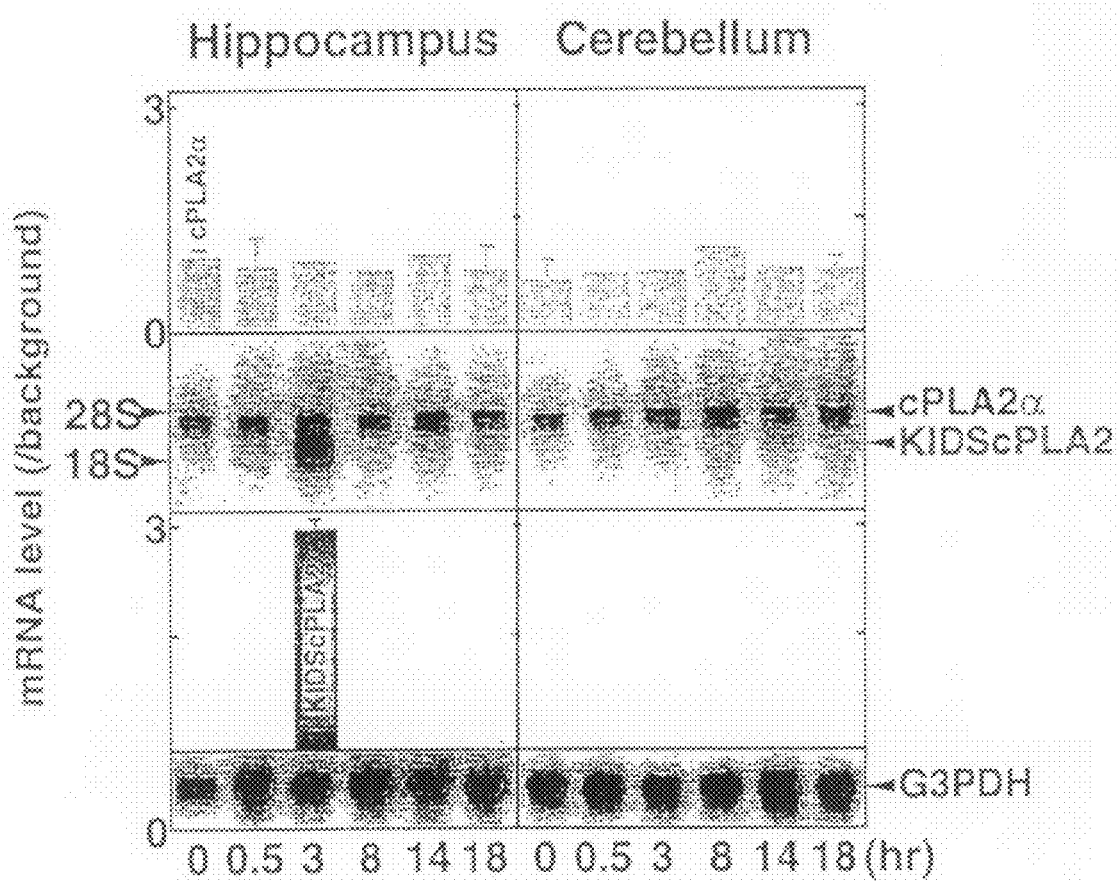
FIG. 2 is a picture (as a substitute for a drawing) showing the result where hippocampus and cerebellum were subjected to a northern blotting with a lapse of time. The left side of FIG. 2 is hippocampus while the right side thereof is cerebellum. In each of them are shown the blots after 0 hour, 0.5 hour, 3 hours, 8 hours, 14 hours and 18 hours from the kainic acid treatment.

Then, a northern blotting was carried out with a lapse of time for hippocampus and cerebellum. The result is shown by a picture in FIG. 2 as a substitute for a drawing. The left side of FIG. 2 is for hippocampus while the right side thereof is for cerebellum. Each of them shows the blots after 0 hour, 0.5 hour, 3 hours, 8 hours, 14 hours and 18 hours from the kainic acid treatment. At any place of FIG. 2, plot was found at the position of cPLA2α while, only at the area after 3 hours from the kainic acid treatment in the case of hippocampus (left side of FIG. 2), there were observed plots of shorter chain length not only at the position of cPLA2α but also beneath that.

Figure 3:
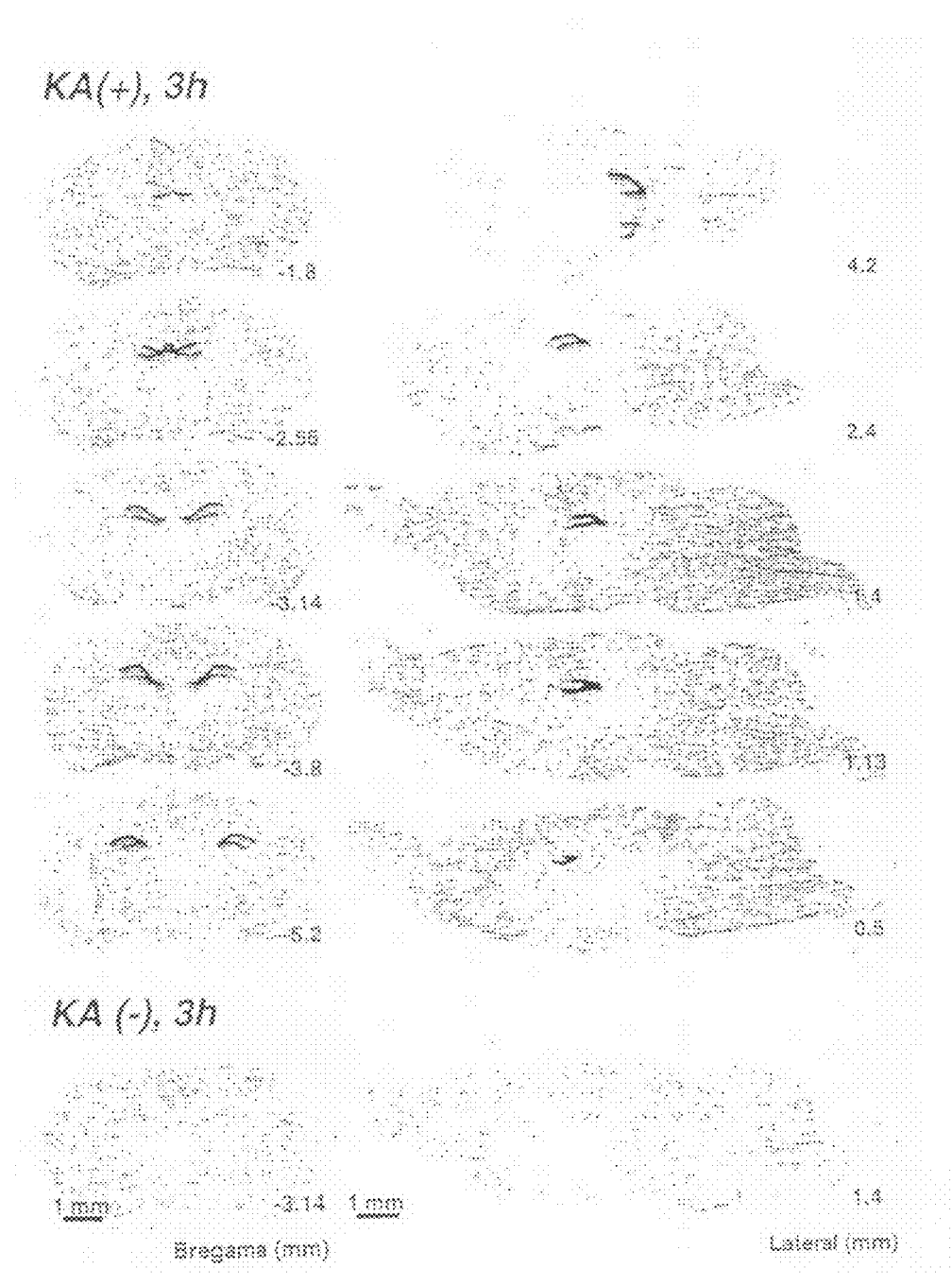

When an in situ hybridization was further carried out, a specific expression was noted at dentate gyrus of hippocampus. The result is shown by a picture in FIG. 3 as a substitute for a drawing. The left side of FIG. 3 is the result of a cross section of the brain while the right side thereof is that from a vertical section of the brain. In FIG. 3, the part which is in black is a colored part. The colored part is dentate gyrus of hippocampus.

Figure 4:
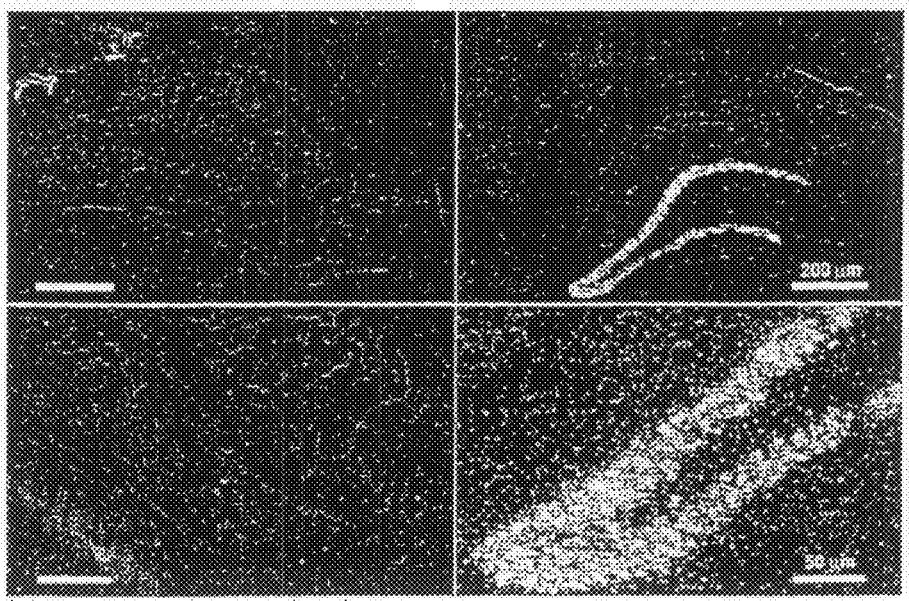
FIG. 4 is a picture (as a substitute for a drawing) where the part of dentate gyrus of hippocampus in the result of FIG. 3 is enlarged. The left side of FIG. 4 is the result where no kainic acid treatment was carried out while the right side thereof is that after 3 hours from the kainic acid treatment.
Figure 4:
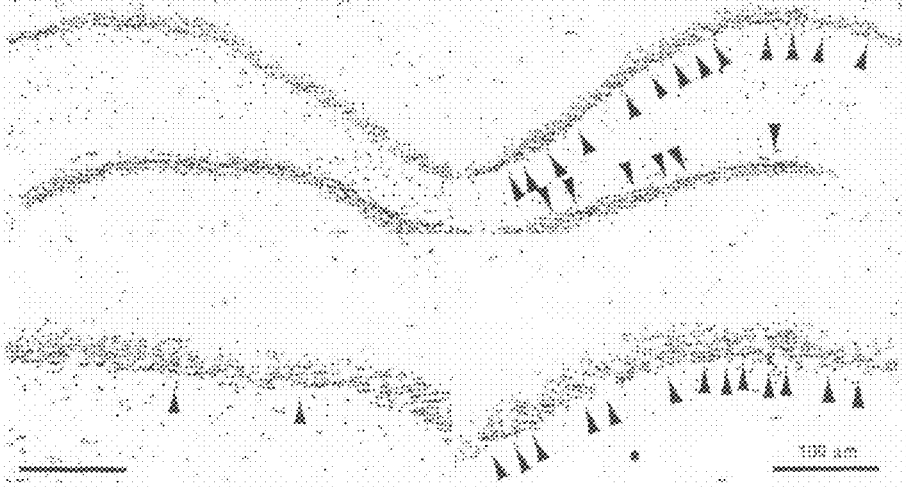

The result is enlarged and is shown in FIG. 4 which is a picture as a substitute for a drawing. The left side of FIG. 4 is the result where no kainic acid treatment was carried out while the right side thereof is that after 3 hours from the kainic acid treatment. Coloration was able to be observed around the dentate gyrus of hippocampus. This coloration was strong at the outside of the dentate gyrus of hippocampus and, in the dentate gyrus of hippocampus, there are many nerve stem cells whereby that is presumed to be due to the nerve stem cells existing in the dentate gurus of hippocampus.

Therefore, the full length of cPLA2 was used as a probe and the desired cDNA was obtained from a library of dentate gyrus of hippocampus. This cDNA was translated into protein and its enzymatic activity was checked whereupon a phospholipase A2 activity was found.

From the structure analysis, that was found to be a phospholipase A2 molecule of a shortened type of phospholipase A2 of a cytoplasmic type (cytosolic phospholipase A2; abbreviated as cPLA2). cDNA of rat was a protein with a molecular weight of 50,810.6 comprising 445 amino acids having 1,842 base pairs where the translated region was 1,355 base pairs. Since this phospholipase A2 of a shortened type is specifically expressed in the dentate gyrus of hippocampus after stimulation with kainic acid, it was named a kainate-inducible dentate gyrus specific cPLA2 (KIDS cPLA2).

Amino acid sequence of the resulting KIDS cPLA2 is shown by way of one-letter code of amino acid as follows.

KIDS cPLA2 of human being is as follows.

| | |
|---|---|
| MNTTLSSLKEKVNTAQCPLP | 20 |
| LFTCLHVKPDVSELMFADWV | 40 |
| EFSPYEIGMAKYGTFMAPDL | 60 |
| FGSKFFMGTVVKKYEENPLH | 80 |
| FLMGVWGSAFSILFNRVLGV | 100 |
| SGSQSRGSTMEEELENITTK | 120 |
| HIVSNDSSDSDDESHEPKGT | 140 |
| ENEDAGSDYQSDNQASWIHR | 160 |
| MIMALVSDSALFNTREGRAG | 180 |
| KVHNFMLGLNLNTSYPLSPL | 200 |
| SDFATQDSFDDDELDAAVAD | 220 |
| PDEFERIYEPLDVKSKKIHV | 240 |
| VDSGLTFNLPYPLILRPQRG | 260 |
| VDLIISFDFSARPSDSSPPF | 280 |
| KELLLAEKWAKMNKLPFPKI | 300 |
| DPYVFDREGLKECYVFKPKN | 320 |
| PDMEKDCPTIIHFVLANINF | 340 |
| RKYKAPGVPRETEEEKEIAD | 360 |
| FDIFDDPESPFSTFNFQYPN | 380 |
| QAFKRLHDLMHFNTLNNIDV | 400 |
| IKEAMVESIEYRRQNPSRCS | 420 |
| VSLSNVEARRFFNKEFLSKP | 440 |
| KA | 442 |

KIDS cPLA2 of rat is as follows.

| | |
|---|---|
| MSTTLSSLKEKVSAARCPLP | 20 |
| LFTCLHVKPDVSELMFADWV | 40 |
| EFSPYEIGMAKYGTFMTPDL | 60 |
| FGSKFFMGTVVKKYEENPLH | 80 |
| FLMGVWGSAFSILFNRVLGV | 100 |
| SGSQNKGSTMEEELENITAK | 120 |
| HIVSNDSSDSDDEAQGPKGT | 140 |
| ENEDAEREYQNDNQASWVHR | 160 |
| MLMALVSDSALFNTREGRAG | 180 |
| KEHNFMLGLNLNTSYPLSPL | 200 |
| RDFSPQDSFDDDELDAAVAD | 220 |
| PDEFERIYEPLDVKSKKIHV | 240 |
| VDSGLTFNLPYPLILRPQRG | 260 |
| VDLIISFDFSARPSDTSPPF | 280 |
| KELLLAEKWAKMNKLPFPKI | 300 |
| DPYVFDREGLKECYVFKPKN | 320 |
| PDVEKDCPTIIHFVLANINF | 340 |
| RKYKAPGVLRETKEEKEIAD | 360 |
| FDIFDDPESPFSTFNFQYPN | 380 |
| QAFKRLHDLMYFNTLNNIDV | 400 |
| IKDAIVESIEYRRQNPSRCS | 420 |
| VSLSNVEARKFFNKEFLSKP | 440 |
| TAESI | 445 |

KIDS cPLA2 of mouse is as follows.

| | |
|---|---|
| MSMTLSSLKEKVNAARCPLP | 20 |
| LFTCLHVKPDVSELMFADWV | 40 |
| EFSPYEIGMAKYGTFMAPDL | 60 |
| FGSKFFMGTVVKKYEENPLH | 80 |
| FLMGVWGSAFSILFNRVLGV | 100 |
| SGSQNKGSTMEEELENITAK | 120 |
| HIVSNDSSDSDDEAQGPKGT | 140 |
| ENEEAEKEYQSDNQASWVHR | 160 |
| MLMALVSDSALFNTREGRAG | 180 |
| KVHNFMLGLNLNTSYPLSPL | 200 |
| RDFSSQDSFDDELDAAVADP | 220 |
| DEFERIYEPLDVKSKKIHVV | 240 |
| DSGLTFNLPYPLILRPQRGV | 260 |
| DLIISFDFSARPSDTSPPFK | 280 |
| ELLLAEKWAKMNKLPFPKID | 300 |
| PYVFDREGLKECYVFKPKNP | 320 |
| DVEKDCPTIIHFVLANINFR | 340 |
| KYKAPGVLRETKEEKEIADF | 360 |
| DIFDDPESPFSTFNFQYPNQ | 380 |
| AFKRLHDLMYFNTLNNIDVI | 400 |
| KDAIVESIEYRRQNPSRCSV | 420 |

-continued

SLSNVEARKFFNKEFLSKPT                    440

V                                       441

Amino acid sequence of KIDS cPLA2 of human being is shown in SEQ ID NO: 1 of the Sequence Listing. Base sequence of translated region of cDNA of KIDS cPLA2 of human being is shown in SEQ ID NO: 2, NO: 3 and NO: 4 of the Sequence Listing. SEQ ID NO: 2 is that where the sequence of 5' UTR is made type I, SEQ ID NO: 3 is that where the sequence of 5' UTR is made type II and SEQ ID NO: 4 is that where the sequence of 5' UTR is not classified into type I and type II.

Amino acid sequence of KIDS cPLA2 of rat is shown in SEQ ID NO: 5 of the Sequence Listing. Base sequence of the translated region of cDNA of KIDS cPLA2 of rat is shown in SEQ ID NO: 6 and NO: 7 of the Sequence Listing. SEQ ID NO: 6 is that for type I and SEQ ID NO: 7 is that for type II.

Amino acid sequence of KIDS cPLA2 of mouse is shown in SEQ ID NO: 8 of the Sequence Listing. Base sequence of the translated region of cDNA of KIDS cPLA2 of mouse is shown in SEQ ID NO: 9, NO: 10 and NO: 11 of the Sequence Listing. SEQ ID NO: 9 is that where the sequence of 5' UTR is made type I, ID SEQ NO: 10 is that where the sequence of 5' UTR is made type II and SEQ ID NO: 11 is that where the sequence of 5' UTR is not classified into type I and type II.

Figure 5:
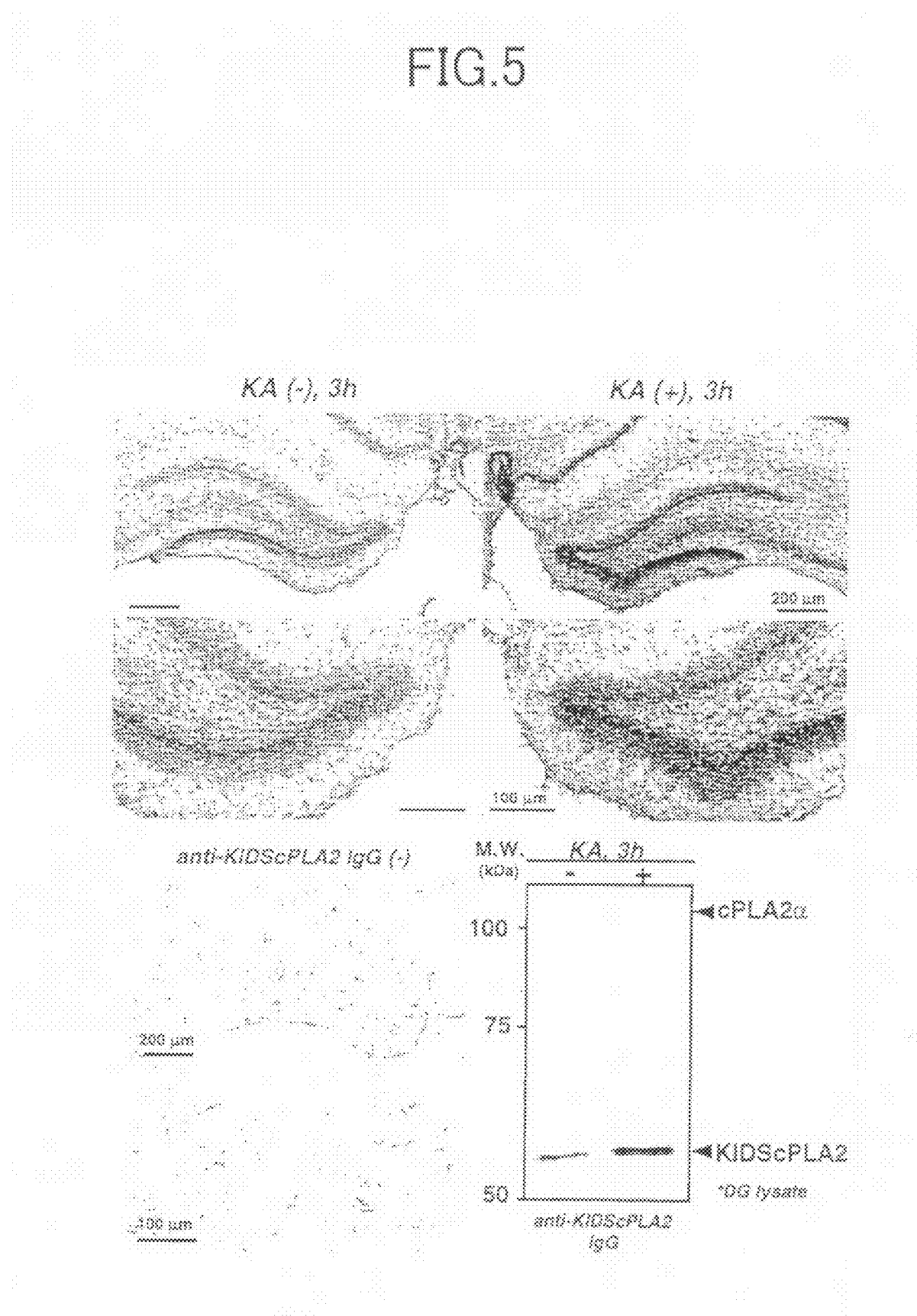
FIG. 5 is a picture (as a substitute for a drawing) showing the result of confirmation of expression of the desired protein by an immunohistochemical analysis using an antibody specifically recognizing KIDS cPLA2 of the present invention. The left side of the upper column of FIG. 5 is the case where no kainic acid treatment was carried out while the right side thereof is the case of 3 hours after the kainic acid treatment. The left side of the lower column of FIG. 5 is the control where no treatment with an anti-KIDS cPLA2 antibody (IgG) was carried out. The right side of the lower column of FIG. 5 is the result of chromatography in the absence of an anti-KIDS cPLA2 antibody (IgG) after 3 hours from the kainic acid treatment ((−) at the left side of the right side, lower column, FIG. 5) and in the presence of that ((+) at the right side thereof).

A polyclone antibody (stump antibody) which specifically recognizes the KIDS cPLA2 of the present invention was prepared. Expression of the desired protein was confirmed by immunohistochemical analysis using that antibody. The result is shown in FIG. 5 which is a picture as a substitute for a drawing. The left side of the upper column of FIG. 5 is the case where no kainic acid treatment was carried out while the right side thereof is the case of 3 hours after the kainic acid treatment. Colored parts due to the antibody can be observed. The left side of the lower column of FIG. 5 is the control where no treatment with an anti-KIDS cPLA2 antibody (IgG) was carried out. The right side of the lower column of FIG. 5 is the result of chromatography in the absence of an anti-KIDS cPLA2 antibody (IgG) after 3 hours from the kainic acid treatment ((−) at the left side of the right side, lower column, FIG. 5) and in the presence of that ((+) at the right side thereof).

Figure 6:
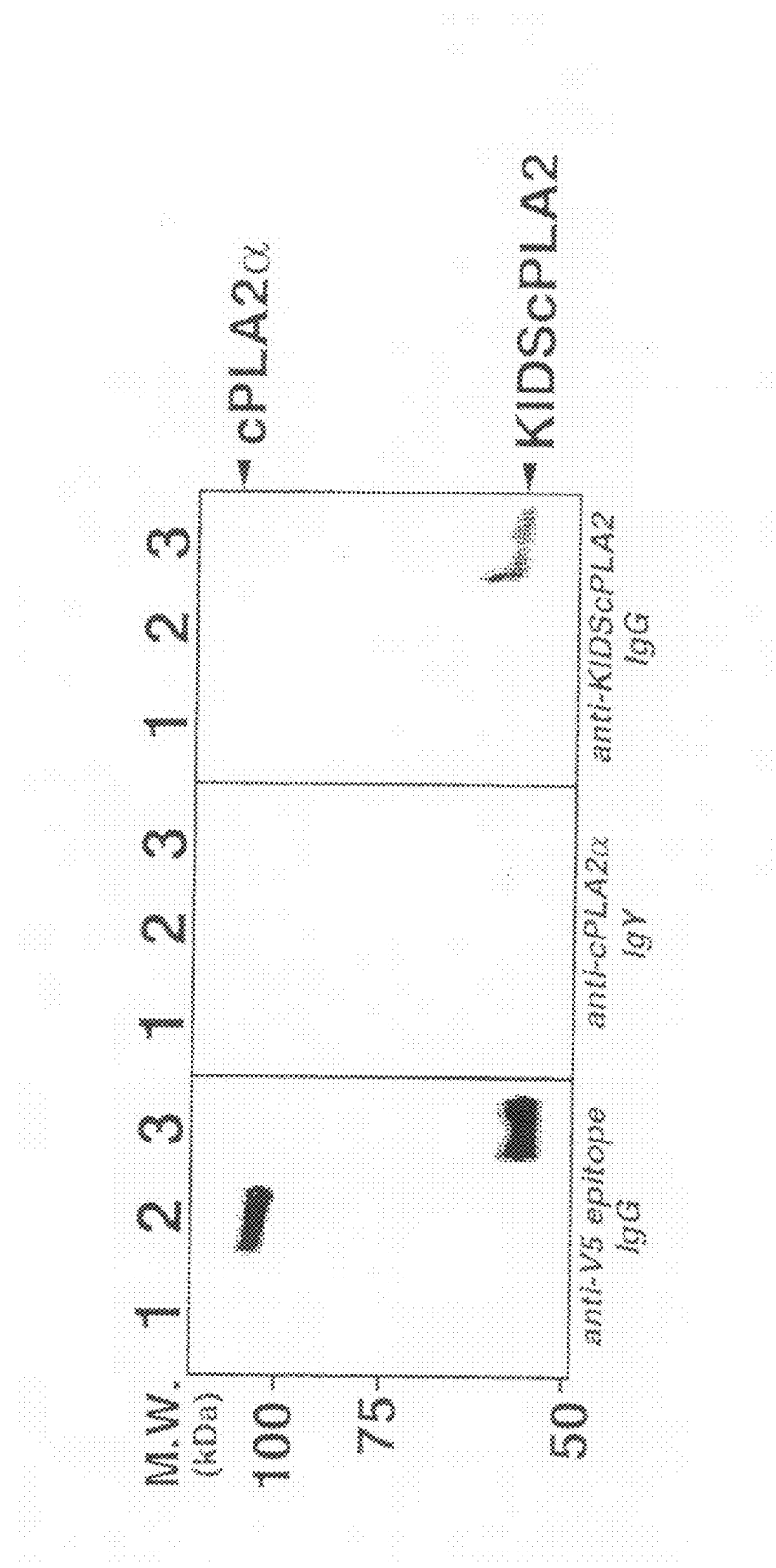
FIG. 6 is a picture (as a substitute for a drawing) showing the result of investigation of expression after integration of cDNA coding for cPLA2α and KIDS cPLA2 of the present invention with an expression vectorpTracerEF.

Then, cDNA coding for KIDS cPLA2 of the present invention and cPLA2 was integrated with an expression vector pTracer EF and its expression was investigated. The result is shown in FIG. 6 which is a picture as a substitute for a drawing. In FIG. 6, the lane 1 is the case of a control vector, the lane 2 is the case of cPLA2α/pTracer EF and the lane 3 is the case of KIDS cPLA2/pTracer EF. In FIG. 6, the left side is the case where an anti-V5 epitope IgG was used, the middle is the case where an anti-cPLA2α IgY was used and the right side is the case where an anti-KIDS cPLA2 IgG was used.

Each spot by the anti-V5 epitope IgG and spot of KIDS cPLA2 by the anti-KIDS cPLA2 IgG were confirmed whereby expression of KIDS cPLA2 was confirmed.

Figure 7:
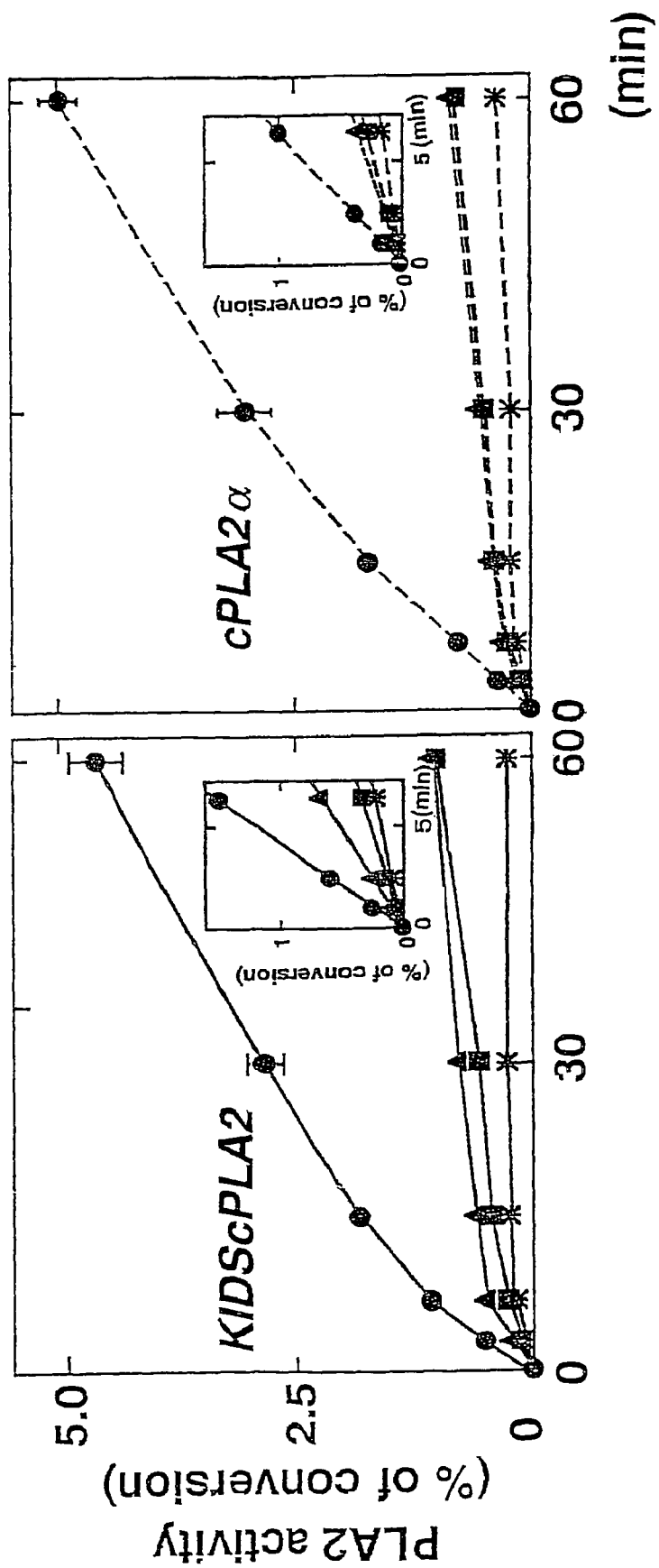
FIG. 7 shows the result of enzymatic activity of KIDSc-PLA2 and cPLA2α of the present invention.

Then enzymatic activity of cPLA2α and KIDS cPLA2 of the present invention were investigated. There were used 1-Pam-2-[$^{14}$C]arachidonoyl-PC (black dots (●) in FIG. 7), 1-Pam-2-[$^{14}$C]linoleoyl-PC (black triangles (▲) in FIG. 7), 1-Pam-2-[$^{14}$C]oleoyl-PC (black squares (■) in FIG. 7) and 1-Pam-2-[$^{14}$C]palmitoyl-PC (asterisks (*) in FIG. 7) as the substrates for testing the enzymatic activity of each of them. The result is shown in FIG. 7. In FIG. 7, the left side is that for KIDS cPLA2 of the present invention while the right side is that for cPLA2α. Each and any of the enzymes showed very high enzymatic activity to arachidonic acid phospholipids and was found to have nearly the same activity as phospholipase A2.

Values of those enzymatic activities (pmol/minute) are shown in the following Table 1.

TABLE 1

Enzymatic Activities of KIDS cPLA2 and cPLA2α

| Substrate | Phospholipase A2 Activity (pmol/min) | |
| --- | --- | --- |
|  | KIDS cPLA2 | cPLA2α |
| 1-Pam-2-[$^{14}$C]arachidonoyl-PC | 35.6 ± 3.8 | 24.4 ± 1.4 |
| 1-Pam-2-[$^{14}$C]linoleoyl-PC | 20.1 ± 1.7 | 11.9 ± 1.8 |
| 1-Pam-2-[$^{14}$C]oleoyl-PC | 14.3 ± 1.5 | 9.1 ± 1.1 |
| 1-Pam-2-[$^{14}$C]palmitoyl-PC | 9.4 ± 1.0 | 9.8 ± 1.7 |

Incidentally, the phospholipase A2 activity is given in terms of the difference from the control.

Then, calcium dependency of cPLA2α and KIDS cPLA2 of the present invention on enzymatic activity was investigated using 1-Pam-2-[$^{14}$C]arachidonoyl-PC as a substrate. EDTA-Ca was used as a calcium source.

Figure 8:
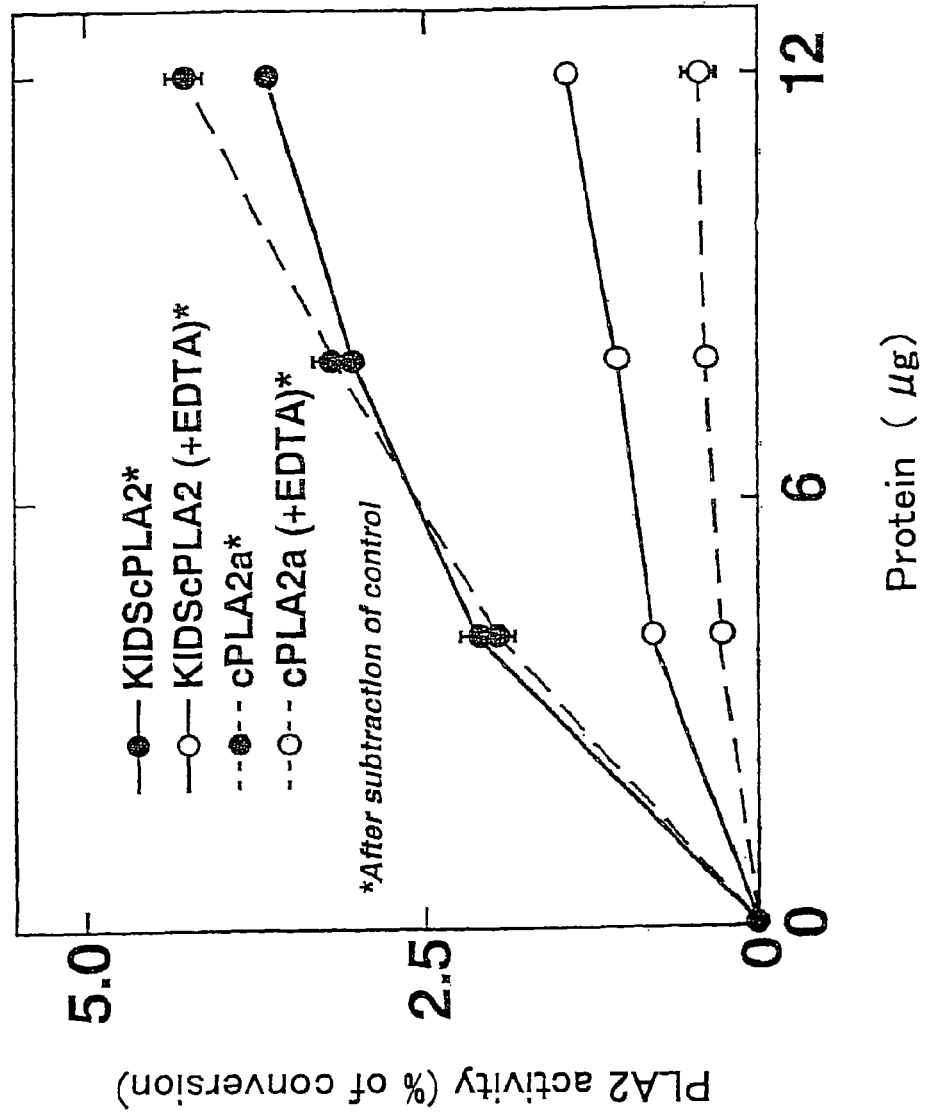
FIG. 8 shows the result of the test of calcium dependency of KIDS cPLA2 and cPLA2α of the present invention on enzymatic activity using 1-Pam-2-[$^{14}$Cys]arachidonoyl-PC as a substrate. The solid lines in FIG. 8 are the case of KIDS cPLA2 of the present invention while the broken lines therein are the case of cPLA2α. In each of them, the black dots (●) are the data in the absence of EDTA Ca while the open circles (○) are those in the presence of EDTA Ca.
Figure 9:
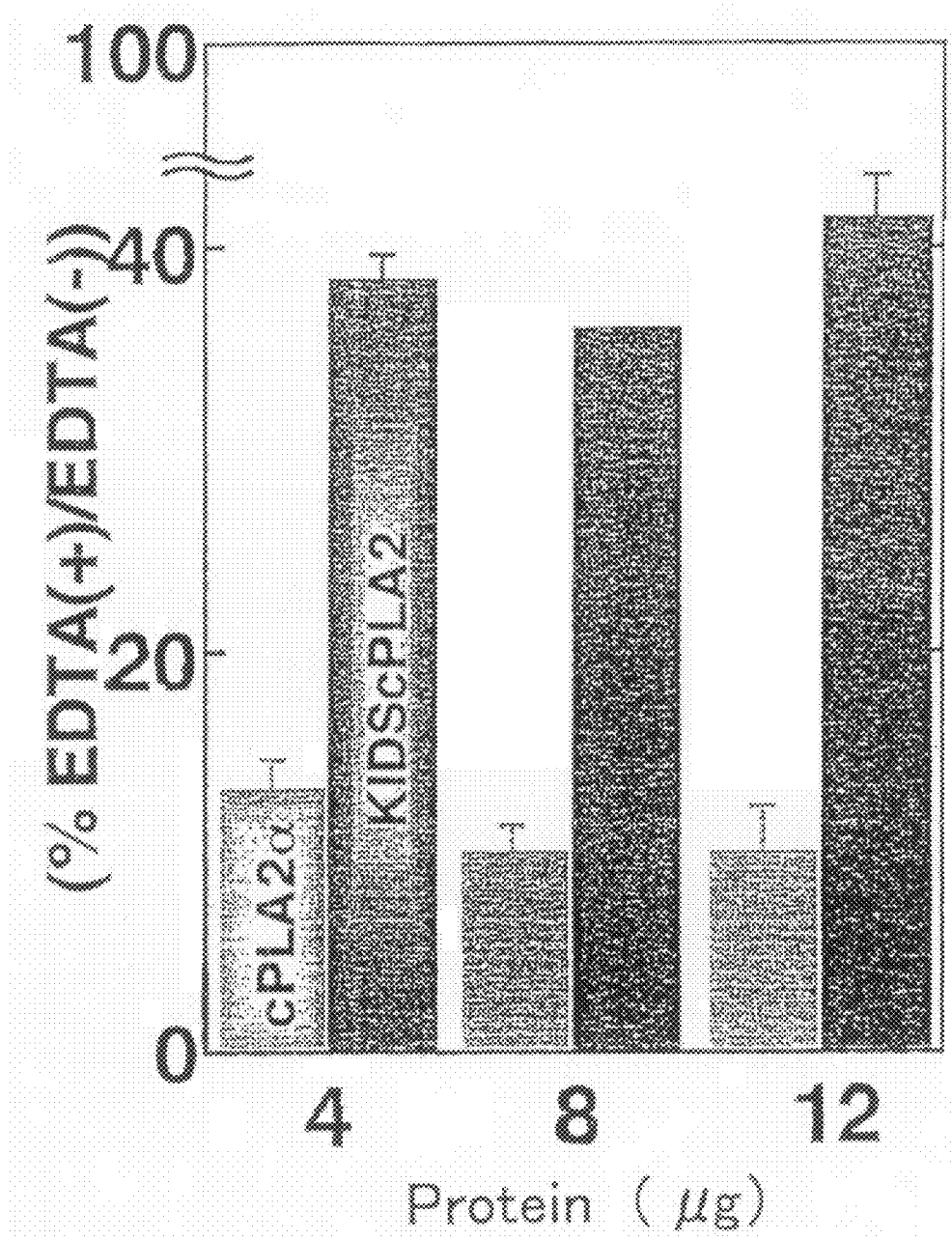
FIG. 9 shows the result given in the above FIG. 8 in terms of a relative ratio.

The result is shown in FIG. 8 and FIG. 9. The solid lines in FIG. 8 are the case of KIDS cPLA of the present invention while the broken lines therein are the case of cPLA2α. In each of them, the black dots (●) are the data in the absence of EDTA-Ca while the open circles (○) are those in the presence of EDTA-Ca. It is noted that, in the case of cPLA2α, there is a sudden reduction in the activity by the presence of calcium while, in the case of KIDS cPLA2 of the present invention, there is no such a reduction in the activity.

FIG. 9 shows the above-mentioned result in terms of a relative ratio. It is noted that, in the case of KIDS cPLA2 of the present invention, an activity of around 40% is maintained even in the presence of calcium while, in the case of cPLA2α, the activity is reduced to an extent of around 10-15% in the presence of calcium.

As such, KIDS cPLA2 of the present invention is characteristic in being calcium-independent as compared with the conventional cPLA2α.

Figure 10:
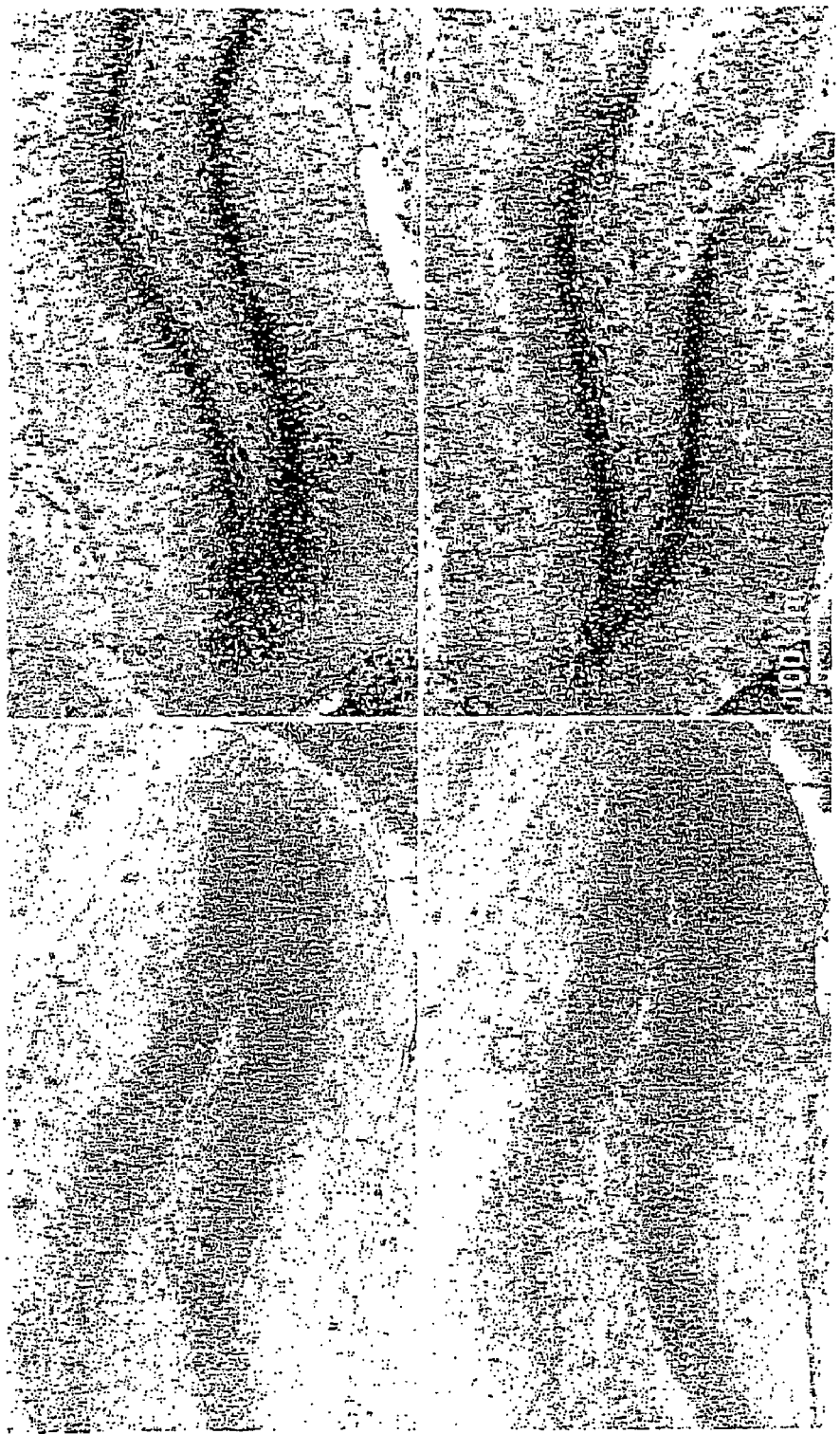
FIG. 10 is a picture (as a substitute for a drawing) showing the result of investigation of expression of KIDS cPLA2 of the present invention in a mouse defective of cPLA.

Then expression of KIDS cPLA2 of the present invention in cPLA-defective mouse prepared by Shimizu, et al. (Uozumi, N. et al., *Nature,* 390, 618-622, 1997) was investigated. The result is shown in FIG. 10 which is a picture as a substitute for a drawing. In FIG. 10, the upper column is that for (+/+) of a knockout mouse while the lower column is that for (−/−) of a knockout mouse. In FIG. 10, the left side is that where no kainic acid treatment was carried out (KA (−)) while the right side is that after 3 hours from the kainic acid treatment (KA (+)). In any of the knockout mice, expression of the present enzyme was able to be confirmed by a kainic acid treatment.

The above shows that KIDS cPLA2 of the present invention expresses using a promoter which is different from its full-length cPLA2.

Figure 11:
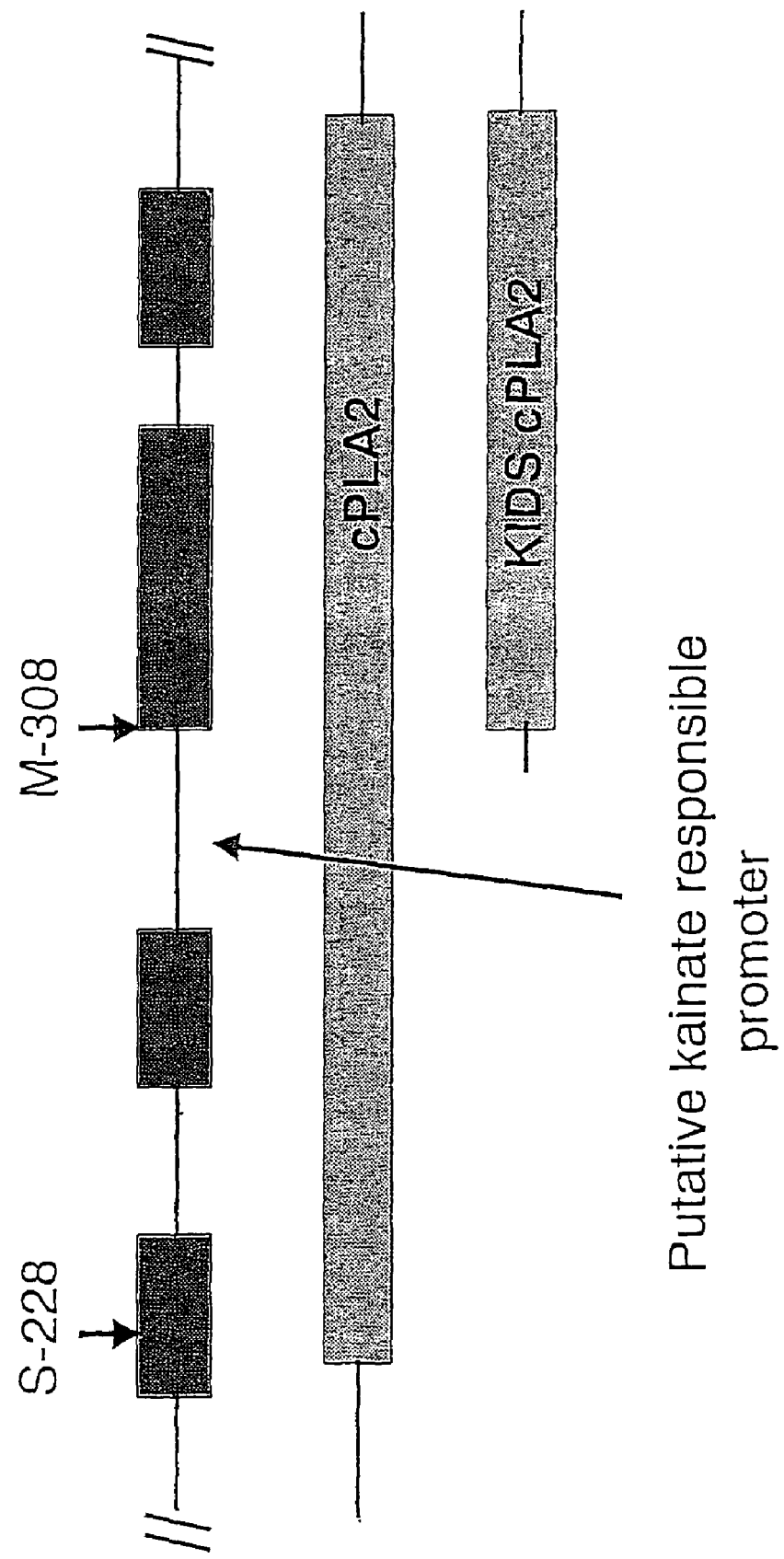
FIG. 11 illustrates the state of expression of cPLA2 and KIDS cPLA2.

FIG. 11 illustrates the state of expression of cPLA2 and KIDS cPLA2. In FIG. 11, the upper column schematically shows exon and intron of cPLA2 in genomic gene. The full-length cPLA2 is produced from all exons and regulatory gene containing a promoter region is present in the upper stream of the initial exon. On the contrary, KIDS cPLA2 of the present invention is a protein starting from the 308th methionine mentioned as "M-308" in FIG. 11 and, since expression of this protein was confirmed in the cPLA-defective mouse, i.e., a mouse where the function of regulatory gene containing a promoter region in the upper stream of the initial exon, it has been found that KIDS cPLA2 of the present invention has a regulatory gene region containing a promoter region in the upper stream of "M-308". However, the said regulatory gene is in such a manner that, under an ordinary state, the gene does not function and has also been noted to function only by the stimulation such as by a kainic acid stimulation.

Therefore, a base sequence of upper stream of "M-308" was analyzed for rat, mouse and human being. The result is aligned and shown in FIG. 12.

The base sequence of this intron in human being is shown in SEQ ID NO: 12 of the Sequence Listing. The base sequence thereof in rat is shown in SEQ ID NO: 13 of the Sequence Listing. Further, the base sequence thereof in mouse is shown in SEQ ID NO: 14 of the Sequence Listing.

Figure 12:
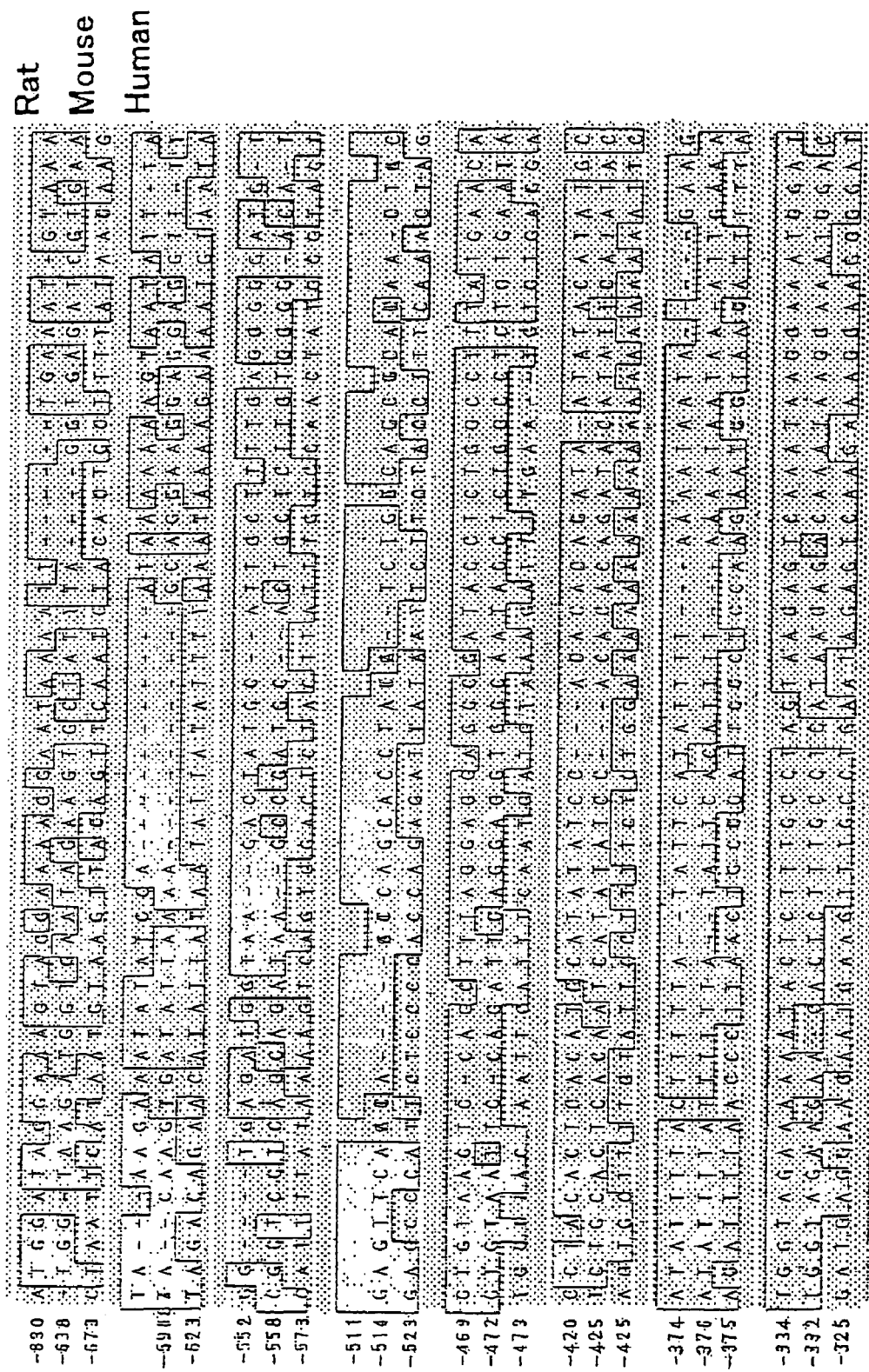
FIG. 12 shows a numbering for a base sequences from the first base of intron immediately before exon containing "Met-308" of rat (upper column), mouse (middle column) and human being (lower column) in which the base wherefrom an exon region of the full-length cPLA2 starts is named 1. The rat sequence is represented by SEQ ID NO: 13 (nucleotides 1 to 630 of SEQ ID NO: 13 correspond to rat nucleotides −630 to −1 of FIG. 12) and SEQ ID NO: 6 (nucleotides 1 to 130 of SEQ ID NO: 6 correspond to rat nucleotides +1 to +130 of FIG. 12). The mouse sequence is represented by SEQ ID NO: 14 (nucleotides 1 to 739 of SEQ ID NO: 14 correspond to mouse nucleotides −638 to +101) and SEQ ID NO: 9 (nucleotides 107 to 133 of SEQ ID NO: 9 correspond to mouse nucleotides +102 to +128). The human being sequence is represented by SEQ ID NO: 15 (nucleotides 1 to 207 of SEQ ID NO: 15 correspond to human nucleotides −673 to −467 of FIG. 12), SEQ ID NO: 12 (nucleotides 1 to 560 of SEQ ID NO: 12 correspond to nucleotides −466 to +94 of FIG. 12), and SEQ ID NO: 2 (nucleotides 96 to 122 of SEQ ID NO: 2 correspond to nucleotides +95 to +121).

FIG. 12 shows a numbering for base sequences from the first base of intron immediately before exon containing "M-308" of rat (upper column), mouse (middle column) and human being (lower column) in which the base wherefrom an exon region of the full-length cPLA2 starts is named No. 1. ATG from the 92nd one (human being) in this numbering is a translation initiation codon of KIDS cPLA2.

Then, expression of KIDS cPLA 2 of the present invention was investigated using nerve cells in the dentate gyrus of hippocampus of the brain. The result is shown in FIG. 13 which is a picture as a substitute for a drawing.

Figure 13:
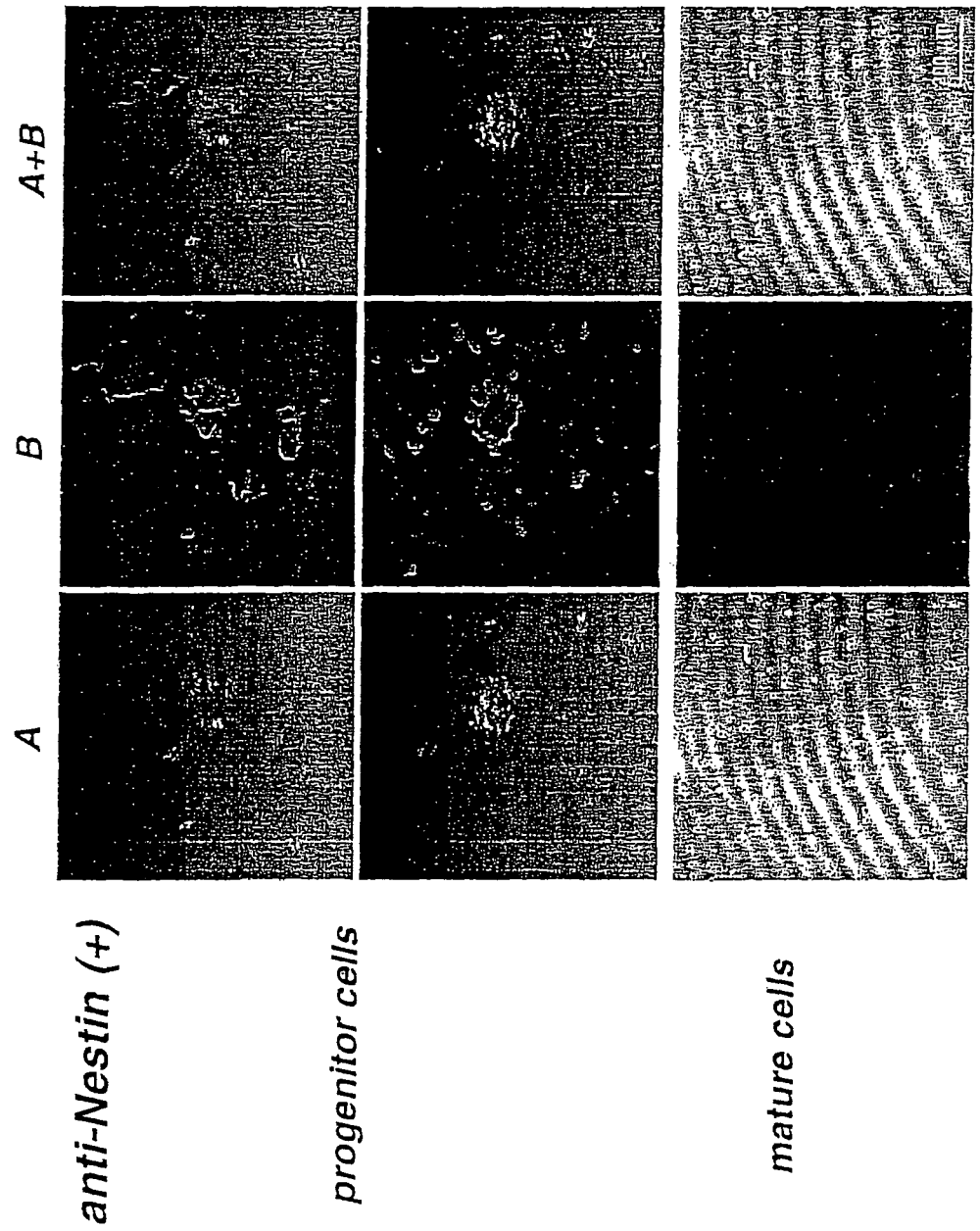
FIG. 13 is a picture (as a substitute for a drawing) showing the result of investigation of expression of KIDS cPLA 2 of the present invention using nerve stem cells and mature nerve cells.

In FIG. 13, the upper column is nestin as a control, the middle column is the case where nerve stem cells were used and the lower column is the case where mature cells of nerve were used. A in the left side shows the positions of each of the cells, B in the middle is coloration showing the expression of KIDS cPLA 2 of the present invention and the right side is that where A at the left side and B at the middle were piled to confirm the positions in both.

As the result, it is noted that no clear expression is observed for KIDS cPLA2 of the present invention in nerve mature cells but a clear expression is observed in nerve stem cells. The above suggests that KIDS cPLA2 of the present invention is a substance which is specifically expressed in nerve stem cells and that, in nerve stem cells, intron in mature cells specifically plays a role of a promoter.

Then expression of KIDS cPLA 2 of the present invention using nerve stem cells by means of stimulation by kainic acid (10 μM), by kainic acid and CNQX (10 μM KA and 20 μM CNQX) and by glutamic acid (50 μM) was investigated.

Figure 14:
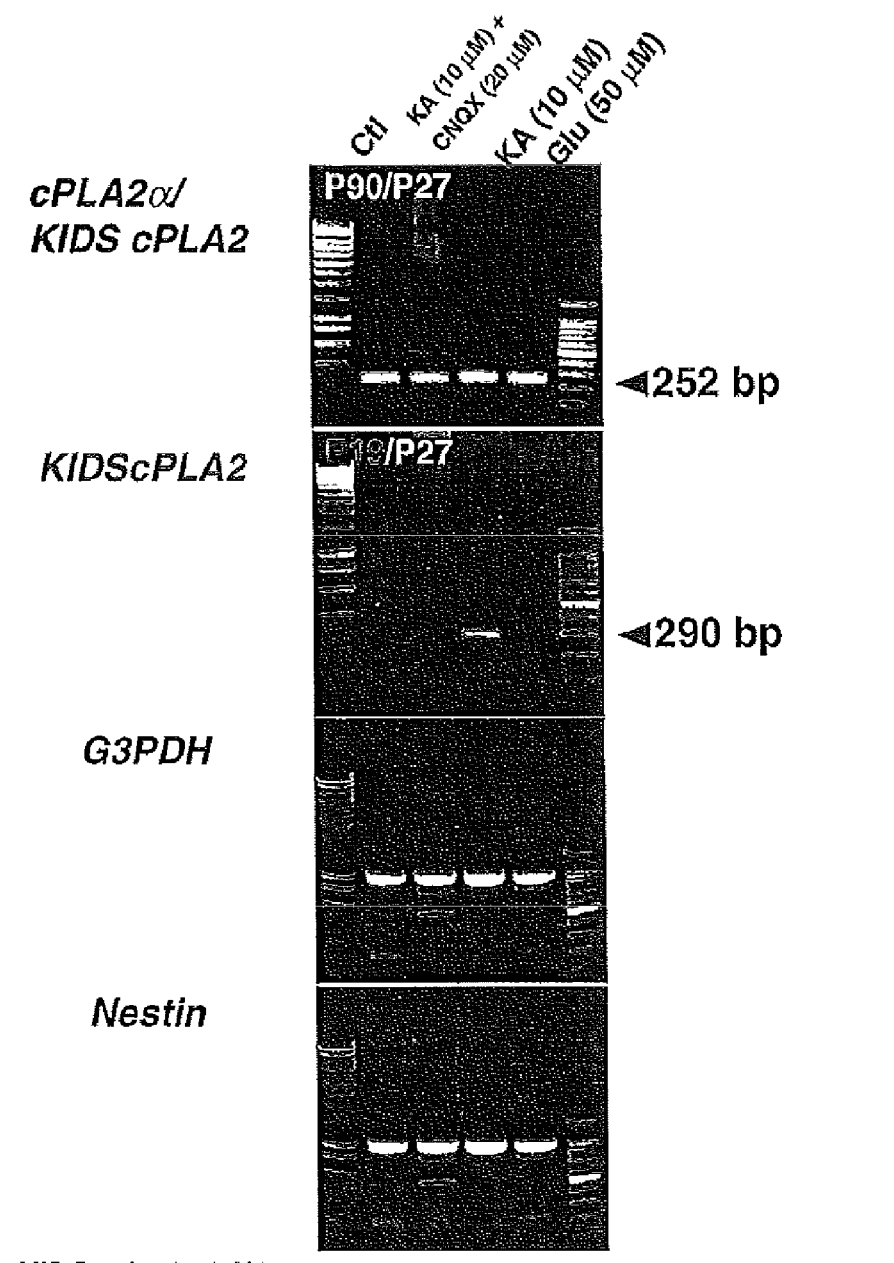
FIG. 14 is a picture (as a substitute for a drawing) showing the result of investigation of expression of KIDS cPLA 2 of the present invention using nerve stem cells by means of stimulation with kainic acid, with kainic acid and CNQX and with glutamic acid.

The result is shown in FIG. 14 which is a picture as a substitute for a drawing. In FIG. 14, the probe used is P90-P27 of 252 bp (the said sequence is a sequence of a moiety which is common in the full-length cPLA2) in the upper column, P19-P27 of 290 bp (the said sequence contains a sequence specific to KIDS cPLA2 of the present invention) in the second column and G3 PDH and nestin in the lower two columns as controls. The lowermost picture of FIG. 14 shows the initiation positions for transcription of KIDS cPLA 2 at the 5'-side and sequential positions of the probes used in the upper two columns in FIG. 14.

The lanes in FIG. 14 are control and stimulations by kainic acid (KA (10 μM)), by kainic acid and CNQX (KA (10 μM)+CNQX (20 μM)) and by glutamic acid (Glu (50 μM)) from the left side.

As a result, in the case of stimulation by kainic acid (10 μM), a specific expression of KIDS cPLA2 of the present invention was confirmed.

Accordingly, the present invention provides a method for searching the nerve stem cells in a specific manner by expression of KIDS cPLA2 of the present invention. Thus, according to such a method of the present invention, cells which are to be the candidates are stimulated by kainic acid and expression of KIDS cPLA2 of the present invention is observed whereby the nerve stem cells are able to be specifically and easily searched.

The KIDS cPLA2 of the present invention is in a partial length of the full-length cPLA2. It is characterized in maintaining a phospholipase A2 activity and having a calcium-independent property and is not always limited to that having an amino acid sequence described in SEQ ID NO: 1, NO: 5 or NO: 8 of the Sequence Listing. So far as it maintains the phospholipase A2 activity and is calcium-independent, about 1-200 or preferably about 1-100, 1-50 or 1-20 amino acid(s) described in SEQ ID NO: 1, NO: 5 or NO: 8 of the Sequence Listing may be substituted with other amino acid(s) or may be deleted therefrom or added thereto. It is also possible that such substitution, deletion and addition may be simultaneously carried out in a combined manner.

Although the KIDS cPLA2 of the present invention may be manufactured according to a process disclosed in the present specification, it may also be manufactured by a conventional gene recombination technique using cDNA of the KIDS cPLA2 of the present invention.

When a full length or a part of the KIDS cPLA2 of the present invention or, preferably, a peptide comprising 10 or more amino acids is used as an antigen, it is possible to manufacture an antibody thereto. The antibody of the present invention may be manufactured by a conventional process and, if necessary, it is possible to manufacture a polyclonal antibody or a monoclonal antibody.

It has been also known that cell death specific to the dentate gyrus of hippocampus takes place by a kainic acid stimulation, by a fit of epilepsy, etc. The present inventors have found that KIDS cPLA2 is expressed in the dentate gyrus of hippocampus by a kainic acid stimulation, by a fit of epilepsy, etc. In view of the above, cell death in the dentate gyrus of hippocampus can be prevented by preparing an inhibitor for the said enzyme and the said enzyme is useful for a development of such an inhibitor as well.

Further, the present inventors have found for the first time that some of intron has a function as a regulatory gene which is activated by an external stimulation and have clarified that at least a base sequence which also functions as a promoter responding to the external stimulation is present in the base sequence of intron.

Accordingly, the present invention provides a gene having a base sequence existing in intron where the said base sequence is able to make the initiation of transcription of RNA by external stimulation possible. The said gene of the present invention comprises at least six bases. Preferably, it is an oligonucleotide having a base sequence existing in intron and comprising at least four or, preferably, at least six bases in the base sequence shown in SEQ ID NO: 12, NO: 13 or NO: 14 of the Sequence Listing where the said base sequence is able to make the initiation of transcription of RNA by external stimulation possible.

Since the said gene of the present invention has a function at least as a promoter participating in initiation of transcription of RNA, the present invention also provides a promoter comprising the said gene or its partial length and being able to make the initiation of transcription of RNA by external stimulation possible. The promoter of the present invention is characterized in that it does not generate the initiation of transcription of RNA under an ordinary condition of mature cells but is able to generate the initiation of transcription of RNA only by a specific external stimulation. The promoter of the present invention is also characterized in that its base sequence is a base sequence existing in intron. More preferably, it is characterized in that the site whereby the initiation of transcription of RNA is made possible is specific. It is preferred that the promoter of the present invention has a length of at least 4-20 bases or, preferably, at least 6-20 bases although the present invention is not limited thereto.

Although the promoter of the present invention may be used solely, it is preferred to use it together with a regulatory element such as an enhancer. Although the regulatory enhancer is positioned at cis, it may be at trans as well. The present invention provides a regulatory gene in which the regulatory element and the promoter of the present invention as mentioned above are in a set. When the regulatory element is a cis-element, such a regulatory gene may be in single-stranded or may be in double-stranded. It is used as double strands when the regulatory element is a trans-element.

When an intron is known to have a base sequence which makes the initiation of transcription of RNA by external stimulation possible while it is not well known that which base sequence in the intron plays a role as a promoter, etc., then the full length of the said intron may be used as a regulatory gene of the present invention.

The term "external stimulation" used in the present invention is a stimulation which does not take place under the growth condition of ordinary mature cells and, preferably, it is a stimulation by which cell death is induced. Thus, there may be exemplified stimulation by a chemical substance such as kainic acid; physical stimulation such as electric shock, temperature change, etc.; stimulation by disorder of other organs such as a fit of epilepsy; and the like.

The term "site-specific" used in the present invention means that a thing is specific to a site which is able to be discriminated from others in terms of type, state, growth degree, etc. of tissues, organs or cells in living body. Although the promoter, gene, etc. of the present invention which are able to make the initiation of transcription of RNA by external stimulation possible may not be always site-specific, they may be site-specific as well. The base sequence of intron shown by SEQ ID NO: 12, NO: 13 and NO: 14 of the Sequence Listing of the present specification is believed to be specific to the dentate gyrus of hippocampus although the promoter, gene, etc. of the present invention is not limited thereto.

The present invention is to clarify the presence of a base sequence which makes the initiation of transcription of RNA by external stimulation in intron of living thing possible and the range of utilization of such a gene of the present invention is quite broad. The first characteristic is that, since it is present as intron, even when the gene is introduced, it usually functions only as intron and does not affect the ordinary growth of living things. The second characteristic is that the regulatory gene of the present invention is inactive for the transcription of RNA under an ordinary state and does not express the protein coded at its downstream. The third characteristic is that it is also possible to make it expressed in a site-specific manner.

Since the promoter and regulatory gene of the present invention have such characteristics, applications according to the particular object are possible. For example, when it is an object that a partial length of a protein is expressed whereby its physiological activity is observed in vivo, the gene of the present invention is introduced immediately before the exon containing methionine which is to be an initiation codon to give an external stimulation to living body whereby expression of protein having a desired partial length can be promoted. When there is no suitable methionine, it may be also possible to introduce a base sequence coding for methionine into an intron region.

According to the second characteristic, gene bonded with the regulatory gene and promoter of the present invention at the upper stream of the desired protein is introduced into living body to give a specific external stimulation whereby the expression of the desired introduced protein is expressed only at the stage of giving the external stimulation. For example, it is possible that a physiologically active protein is added to the end of the promoter of the present invention and, only when a specific external stimulation is applied, the said physiologically active protein is expressed and the said physiological activity is temporarily given to the cell. When a toxin such as diphtheria toxin is used as a physiologically active protein, it is now possible to kill the cells in a transient manner. Alternatively, the gene to which CRE gene is connected to the downstream of the promoter of the present invention is introduced whereupon there is prepared a transgenic mouse where specific gene such as glutamic acid receptor is surrounded by a lox-P sequence. By doing so, CRE gene is expressed and specific gene such as glutamic acid receptor surrounded by a lox-P sequence is deleted by a homologous recombination when a specific external stimulation is applied and, therefore, it is possible to prepare a mouse deficient in specific gene such as a glutamic acid receptor as from the stage of application of a specific external stimulation. It is now possible by such a transgenic mouse to precisely analyze the pathology in mature living body where specific gene such as a glutamic acid receptor is deficient.

Further, according to the above-mentioned third characteristic, it is possible to bring about the above-mentioned characteristic in a site-specific manner in a living body. For example, it is possible to destroy a specific gene specifically in the dentate gyrus of hippocampus.

Accordingly, the present invention provides a method where expression of gene coding for a protein introduced into a living body using the promoter and regulatory gene of the present invention is regulated by a specific external stimulation. As mentioned already, it is possible according to this method of the present invention that expression length, expression time and expression site of the introduced protein are regulated.

There is no particular limitation as to the protein which is introduced in this method of the present invention provided that it is a protein having any physiological activity and the protein can be introduced in a state of genome or in a state of cDNA. The protein having a physiological activity may be, for example, that which has the so-called physiological activity such as hormones and cytokines, toxin such as diphtheria toxin or that which induces a homologous recombination such as CRE gene.

The present invention also provides a living thing into which the promoter and regulatory gene of the present invention are introduced at the upper stream of the gene coding for protein. The living thing of the present invention is useful as an experimental animal and is applicable, for example, to mouse, rat, rabbit and monkey. It is also possible to apply to plants.

With regard to such experimental animals, there have been developed transgenic mouse, knockout mouse, etc. In a knockout mouse, there has been a demand for development of a conditional targeting method and, as being noted from the fact that a tissue-specifically expressing promoter, a tetracycline-sensitive promoter, etc. have been developed, there has been a demand for development of a promoter which is tissue-specific and stage-specific. The promoter and regulatory gene of the present invention satisfy such requirements and also have a function as intron and, therefore, the promoter and regulatory gene of the present invention can be widely applied to experimental animals.

EXAMPLES

Now the present invention will be illustrated in more detail by way of the following Examples although the present invention is not limited to those Examples only.

Example 1

Northern Blotting Using Various Probes of cPLA2 cDNA of cPLA2a of rat was divided into four main region, i.e., A, B, C and D from the 5'-terminal. Length of each region was made around 300-500 bp and, after such a cDNA fragment was integrated with a riboprobe synthetic vector, a radio-labeled riboprobe was synthesized by an in vitro transcription method. A hybridization reaction was carried out using a membrane which was blotted with poly(A)$^+$RNA of hippocampal dentate gyrus and hippocampus of rat subjected to a kainic acid stimulation and a riboprobe of each of A, B, C and D to check which probe was able to detect the KIDS cPLA2. As a result, it was found that KIDS cPLA2 mRNA was detected in riboprobes of B, C and D except A.

The result is shown in FIG. 1 and FIG. 2.

Example 2

In Situ Hybridization

Brain of Wister rat of 3 weeks age stimulated by kainic acid was fixed by 4% paraformaldehyde and then a frozen slice was prepared. Each of the radio-labeled riboprobes B, C and D was subjected to a hybridization reaction with the frozen slice and the labeled image of the slice from each probe was confirmed to be same. Then, frozen slice of the brain was prepared again using riboprobe C with or without a kainic acid stimulation and an expression pattern of KIDS cPLA2 mRNA was investigated. As a result, KIDS cPLA2 mRNA was found to be drastically induced in the hippocampal dentate gyrus. When a strongly enlarged image was observed under a microscope, KIDS cPLA2 mRNA was found to express particularly abundantly in the innermost layer of the dentate gyrus.

The result is shown in FIG. 3 and FIG. 4.

Example 3

Immunohistochemical Dyeing

Brains of cPLA2a knockout mouse and C57/Black 6J mouse of 6-10 weeks age and Wister rat of 3 weeks age stimulated by kainic acid were fixed with 4% paraformaldehyde and then frozen slices were prepared. Immunoreaction of an anti-KIDS cPLA2-specific stump antibody with the brain slice was carried out overnight at 4° C. and expression of KIDS cPLA2 protein was confirmed by a secondary antibody labeled with gold colloid. As a result, it was found that, like mRNA, KIDS cPLA2 was drastically induced in the hippocampal dentate gyrus and further that such an expression was noted in the hippocampal dentate gyrus of cPLA2a knockout mouse as well. From the above, it was suggested that a promoter of KIDS cPLA2 was present at the downstream of the eighth exon of cPLA2a destroyed by a cPLA2a knockout mouse and found that an isoform of cPLA2a was induced by acute nervous stimulation.

The result is shown in FIG. 5.

Example 4

Cloning of cDNA of KIDS cPLA2 of Rat

Clone was isolated after confirming its presence by two kinds of method.

(1) A cDNA library was prepared using poly(A)$^+$RNA purified from hippocampus of rat after stimulation by kainic acid and a positive clone was selected using a cDNA sequence of 1,365 (Rsa I)-1,925 (Bal I) from the initiation point for translation of cPLA2a which is able to detect KIDS cPLA2 as a probe.

From 4,000,000 clones were selected 12 positive clones. Among them, two are those of full-length phospholipase A2 while six and four among the residual ten were different it their type. The former was named type II and the latter was named type I.

(2) In order to confirm the 5'-terminal of KIDS cPLA2 cDNA of rat, a 5' RACE method (5'-rapid amplification of cDNA ends) was carried out using poly(A)$^+$RNA purified from the hippocampus of rat after stimulation by kainic acid. A sequence amplified to the 5'-upper stream from the primer existing in the above-mentioned sequence of 1,365 (Rsa I)-1, 925 (Bal I) was identical with a sequence of clone selected from the cDNA library.

From the above, KIDS cPLA2 was found to be a novel gene induced in hippocampus after stimulation by kainic acid.

An amino acid sequence of the resulting KIDS cPLA2 of rat is shown in SEQ ID NO: 5 of the Sequence Listing. Base sequences of translated region of cDNA of KIDS cPLA2 of rat are shown in SEQ ID NO: 6 (type I) and SEQ ID NO: 7 (type II) of the Sequence Listing.

An amino acid sequence of KIDS cPLA2 of mouse is shown in SEQ ID NO: 8 of the Sequence Listing. Base sequences of translated region of KIDS cPLA2 of mouse are shown in SEQ ID NO: 9 (in the case that 5'UTR is defined as type I), in SEQ ID NO: 10 (in the case that 5'UTR is defined as type II) and in SEQ ID NO: 11 (in the case that 5'UTR is not divided into types I and II), respectively, of the Sequence Listing.

An amino acid sequence of KIDS cPLA2 of human being is shown in SEQ ID NO: 1 of the Sequence Listing. Base sequences of translated region of cDNA of KIDS cPLA2 of human being are shown in SEQ ID NO: 2 (when 5'UTR was made type I), SEQ ID NO: 3 (when 5'UTR was made type II) and SEQ ID NO: 4 (when 5'UTR was not divided into types I and II) of the Sequence Listing.

Those sequences are selected from the most appropriate sequences after the cDNA sequences of human being, mouse and rat were subjected to an alignment program at the same time and then applied with the conditions such as the position of initiation of transcription, the position of nucleotide presumed to be the transcription initiation position for each of type I and type II, the junction sequence connecting the sequence of type I and the sequence of type II, the sequence homology as a whole, etc.

Example 7

Manufacture of an Antibody of KIDS cPLA2

In order to specifically detect the KIDS cPLA2 having the entirely same sequence from a sequence of Met-308 of cPLA2a of rat, a synthetic peptide having an amino acid sequence comprising 7 starting from this Met-308 (Amino Acids 1-7 of SEQ ID NO: 5) was immunized to rabbit and its serum fraction was prepared. Further, immunoglobulin (IgG) was purified from this fraction to give a final specimen. Incidentally, this stump antibody was confirmed to specifically recognize not only KIDS cPLA2 of rat but also KIDS cPLA2 of mouse.

Example 8

Analysis of Base Sequence of Intron

Analysis of intron sequences (assumed promoter region) of KIDS cPLA2 of rat and mouse was carried out by the following method.

It was investigated whether a fundamental transcription activity was present for a region ranging up to about 9 kb upstream including 5' UTR of KIDS cPLA2 of rat and mouse (a region until exon of cPLAa destroyed in knockout mouse). Firstly, there was constructed a reporter vector where each of a sequence of about 9 kb of this region, a sequence including about 1,000 bp upstream of 5' UTR, a sequence including about 500 bp having a high homology among human being, rat and mouse and a sequence of about 700 bp including 5' UTR was integrated with the upper stream of luciferase gene. Such a reporter vector was introduced into an incubated cell strain, the supernatant liquid of the cells was prepared and its luciferase activity was measured as an index for a fundamental transcription activity. As a result, a sequence of about 700 bp including 5' UTR was found to have an especially high transcription activity.

The result is shown in FIG. 12. Further, base sequences of the animals are shown in SEQ ID NO: 12 (human being), SEQ ID NO: 13 (rat) and SEQ ID NO: 14 (mouse).

INDUSTRIAL APPLICABILITY

The present invention provides a novel enzyme which is presumed to be a case for cell death specific to the hippocampal dentate gyrus in stimulation by kainic acid, fit of epilepsy, etc. It is now possible to prevent the cell death by preparing an inhibitor of this enzyme.

The present invention also provides a novel enzyme having a phospholipase A2 activity and being calcium-independent.

The present invention further clarifies for the first time that, in intron, there is a function of making the initiation of transcription of RNA by an external stimulation possible. A novel function of intron in genome is elucidated and, at the same time, there is provided a new type of gene which functions as a promoter or as a regulatory gene by an external stimulation. The new type of gene functioning as a promoter or as a regulatory gene according to the present invention not only has a function as intron but also makes the expression of a stage-specific desired gene in response to an external stimulation possible and further makes the expression of the site-specific desired gene depending upon the tissue possible. Consequently, the promoter or the regulatory gene of the present invention is able to be used for the regulation of expression of gene and is applicable to transgenic animals, knockout animals, etc.

The invention claimed is:

1. An isolated promoter consisting of:
the nucleotide sequence of SEQ ID: No. 12,
wherein said promoter initiates transcription of RNA upon a kainic acid stimulation or an electric stimulation and does not initiate transcription of RNA in the absence of the kainic acid stimulation or the electric stimulation.

2. An isolated promoter consisting of:
a nucleotide sequence that hybridizes under highly stringent conditions to the nucleotide sequence complementary to SEQ ID: No. 12 over its entire length,
wherein said promoter initiates transcription of RNA upon a kainic acid stimulation or an electric stimulation and does not initiate transcription of RNA in the absence of the kainic acid stimulation or the electric stimulation.

3. An isolated promoter comprising:
a nucleotide sequence that hybridizes under highly stringent conditions to the nucleotide sequence complementary to SEQ ID: No. 13 over its entire length,
wherein said promoter initiates transcription of RNA upon a kainic acid stimulation or an electric stimulation and does not initiate transcription of RNA in the absence of the kainic acid stimulation or the electric stimulation.

4. An isolated promoter comprising:
a nucleotide sequence that hybridizes under highly stringent conditions to the nucleotide sequence complementary to SEQ ID: No. 14 over its entire length,
wherein said promoter initiates transcription of RNA upon a kainic acid stimulation or an electric stimulation and does not initiate transcription of RNA in the absence of the kainic acid stimulation or the electric stimulation.

5. The isolated promoter according to claim 1, wherein said promoter initiates transcription of RNA upon the kainic acid stimulation and does not initiate transcription of RNA in the absence of the kainic acid stimulation.

6. The isolated promoter according to claim 1, wherein said promoter initiates transcription of RNA upon the electric stimulation and does not initiate transcription of RNA in the absence of the electric stimulation.

7. An isolated promoter comprising:
the nucleotide sequence of SEQ ID: No. 13,
wherein said promoter initiates transcription of RNA upon a kainic acid stimulation or an electric stimulation and does not initiate transcription of RNA in the absence of the kainic acid stimulation or the electric stimulation.

8. The isolated promoter according to claim 7, wherein said promoter initiates transcription of RNA upon the kainic acid stimulation and does not initiate transcription of RNA in the absence of the kainic acid stimulation.

9. The isolated promoter according to claim 7, wherein said promoter initiates transcription of RNA upon the electric stimulation and does not initiate transcription of RNA in the absence of the electric stimulation.

10. The isolated promoter according to claim 7, wherein the isolated promoter consists of the nucleotide sequence of SEQ ID: No. 13.

11. An isolated promoter comprising:

the nucleotide sequence of SEQ ID: No. 14, wherein said promoter initiates transcription of RNA upon a kainic acid stimulation or an electric stimulation and does not initiate transcription of RNA in the absence of the kainic acid stimulation or the electric stimulation.

12. The isolated promoter according to claim 11, wherein said promoter initiates transcription of RNA upon the kainic acid stimulation and does not initiate transcription of RNA in the absence of the kainic acid stimulation.

13. The isolated promoter according to claim 11, wherein said promoter initiates transcription of RNA upon the electric stimulation and does not initiate transcription of RNA in the absence of the electric stimulation.

14. The isolated promoter according to claim 11, wherein the isolated promoter consists of the nucleotide sequence of SEQ ID: No. 14.

* * * * *

SEQUENCE LISTING

```
<160> NUMBER OF SEQ ID NOS: 15

<210> SEQ ID NO 1
<211> LENGTH: 442
<212> TYPE: PRT
<213> ORGANISM: Human

<400> SEQUENCE: 1

Met Asn Thr Thr Leu Ser Ser Leu Lys Glu Lys Val Asn Thr Ala Gln
 1               5                  10                  15

Cys Pro Leu Pro Leu Phe Thr Cys Leu His Val Lys Pro Asp Val Ser
                20                  25                  30

Glu Leu Met Phe Ala Asp Trp Val Glu Phe Ser Pro Tyr Glu Ile Gly
             35                  40                  45

Met Ala Lys Tyr Gly Thr Phe Met Ala Pro Asp Leu Phe Gly Ser Lys
     50                  55                  60

Phe Phe Met Gly Thr Val Val Lys Lys Tyr Glu Glu Asn Pro Leu His
 65                  70                  75                  80

Phe Leu Met Gly Val Trp Gly Ser Ala Phe Ser Ile Leu Phe Asn Arg
                 85                  90                  95

Val Leu Gly Val Ser Gly Ser Gln Ser Arg Gly Ser Thr Met Glu Glu
            100                 105                 110

Glu Leu Glu Asn Ile Thr Thr Lys His Ile Val Ser Asn Asp Ser Ser
        115                 120                 125

Asp Ser Asp Glu Ser His Glu Pro Lys Gly Thr Glu Asn Glu Asp
    130                 135                 140

Ala Gly Ser Asp Tyr Gln Ser Asp Asn Gln Ala Ser Trp Ile His Arg
145                 150                 155                 160
```

```
Met Ile Met Ala Leu Val Ser Asp Ser Ala Leu Phe Asn Thr Arg Glu
            165                 170                 175

Gly Arg Ala Gly Lys Val His Asn Phe Met Leu Gly Leu Asn Leu Asn
            180                 185                 190

Thr Ser Tyr Pro Leu Ser Pro Leu Ser Asp Phe Ala Thr Gln Asp Ser
            195                 200                 205

Phe Asp Asp Asp Glu Leu Asp Ala Ala Val Ala Asp Pro Asp Glu Phe
        210                 215                 220

Glu Arg Ile Tyr Glu Pro Leu Asp Val Lys Ser Lys Ile His Val
225                 230                 235                 240

Val Asp Ser Gly Leu Thr Phe Asn Leu Pro Tyr Pro Leu Ile Leu Arg
            245                 250                 255

Pro Gln Arg Gly Val Asp Leu Ile Ile Ser Phe Asp Phe Ser Ala Arg
            260                 265                 270

Pro Ser Asp Ser Ser Pro Pro Phe Lys Glu Leu Leu Leu Ala Glu Lys
            275                 280                 285

Trp Ala Lys Met Asn Lys Leu Pro Phe Pro Lys Ile Asp Pro Tyr Val
            290                 295                 300

Phe Asp Arg Glu Gly Leu Lys Glu Cys Tyr Val Phe Lys Pro Lys Asn
305                 310                 315                 320

Pro Asp Met Glu Lys Asp Cys Pro Thr Ile Ile His Phe Val Leu Ala
            325                 330                 335

Asn Ile Asn Phe Arg Lys Tyr Lys Ala Pro Gly Val Pro Arg Glu Thr
            340                 345                 350

Glu Glu Glu Lys Glu Ile Ala Asp Phe Asp Ile Phe Asp Asp Pro Glu
            355                 360                 365

Ser Pro Phe Ser Thr Phe Asn Phe Gln Tyr Pro Asn Gln Ala Phe Lys
            370                 375                 380

Arg Leu His Asp Leu Met His Phe Asn Thr Leu Asn Asn Ile Asp Val
385                 390                 395                 400

Ile Lys Glu Ala Met Val Glu Ser Ile Glu Tyr Arg Arg Gln Asn Pro
            405                 410                 415

Ser Arg Cys Ser Val Ser Leu Ser Asn Val Glu Ala Arg Arg Phe Phe
            420                 425                 430

Asn Lys Glu Phe Leu Ser Lys Pro Lys Ala
            435                 440

<210> SEQ ID NO 2
<211> LENGTH: 1908
<212> TYPE: DNA
<213> ORGANISM: Human

<400> SEQUENCE: 2
gattttgatt ggaagtacta ttttgaatag cattctttct gtgtctgttt ataaatttaa      60
agtcatcttt ttctttcttc tgtggacaga gaatgaatac tactctgagc agtttgaagg     120
aaaaagttaa tactgcacaa tgcccttttac ctcttttcac ctgtcttcat gtcaaacctg     180
acgtttcaga gctgatgttt gcagattggg ttgaattag tccatacgaa attggcatgg      240
ctaaatatgg tacttttatg gctcccgact tatttggaag caatttttt atgggaacag      300 tcgttaagaa gtatgaagaa aaccccttgc atttcttaat gggtgtctgg ggcagtgcct     360
tttccatatt gttcaacaga gttttgggcg tttctggttc acaaagcaga ggctccacaa     420
tggaggaaga attagaaaat attaccacaa agcatattgt gagtaatgat agctcggaca     480
gtgatgatga atcacacgaa cccaaaggca ctgaaaatga agatgctgga agtgactatc     540
```

| | |
|---|---|
| aaagtgataa tcaagcaagt tggattcatc gtatgataat ggccttggtg agtgattcag | 600 |
| ctttattcaa taccagagaa ggacgtgctg ggaaggtaca caacttcatg ctgggcttga | 660 |
| atctcaatac atcttatcca ctgtctcctt tgagtgactt tgccacacag gactcctttg | 720 |
| atgatgatga actggatgca gctgtagcag atcctgatga atttgagcga atatatgagc | 780 |
| ctctggatgt caaaagtaaa aagattcatg tagtggacag tgggctcaca tttaacctgc | 840 |
| cgtatccctt gatactgaga cctcagagag gggttgatct cataatctcc tttgactttt | 900 |
| ctgcaaggcc aagtgactct agtcctccgt tcaaggaact tctacttgca gaaaagtggg | 960 |
| ctaaaatgaa caagctcccc tttccaaaga ttgatcctta tgtgtttgat cgggaagggc | 1020 |
| tgaaggagtg ctatgtcttt aaacccaaga atcctgatat ggagaaagat tgcccaacca | 1080 |
| tcatccactt tgttctggcc aacatcaact tcagaaagta caaggctcca ggtgttccaa | 1140 |
| gggaaactga ggaagagaaa gaatcgctga ctttgatat ttttgatgac ccagaatcac | 1200 |
| cattttcaac cttcaatttt caatatccaa atcaagcatt caaaagacta catgatctta | 1260 |
| tgcacttcaa tactctgaac aacattgatg tgataaaaga agccatggtt gaaagcattg | 1320 |
| aatatagaag acagaatcca tctcgttgct ctgtttccct tagtaatgtt gaggcaagaa | 1380 |
| gattttcaa caaggagttt ctaagtaaac ccaaagcata gttcatgtac tggaaatggc | 1440 |
| agcagtttct gatgctgagg cagtttgcaa tcccatgaca actggattta aaagtacagt | 1500 |
| acagatagtc gtactgatca tgagagactg gctgatactc aaagttgcag ttacttagct | 1560 |
| gcatgagaat aatactatta taagttaggt gacaaatgat gttgattatg taaggatata | 1620 |
| cttagctaca ttttcagtca gtatgaactt cctgatacaa atgtagggat atatactgta | 1680 |
| tttttaaaca tttctcacca actttcttat gtgtgttctt tttaaaaatt ttttttcttt | 1740 |
| taaaatattt aacagttcaa tctcaataag acctcgcatt atgtatgaat gttattcact | 1800 |
| gactagattt attcatacca tgagacaaca ctattttat ttatatatgc atatatatac | 1860 |
| atacatgaaa taaatacatc aatataaaaa taaaaaaaaa cggaattc | 1908 |

<210> SEQ ID NO 3
<211> LENGTH: 1925
<212> TYPE: DNA
<213> ORGANISM: Human

<400> SEQUENCE: 3

| | |
|---|---|
| gattattttt taaatgaaga tagttacttc catagagctt attttttgtt gttcattcag | 60 |
| gacctagtaa tttctagaag taataagact tattttatt ataaagagaa tgaatactac | 120 |
| tctgagcagt ttgaaggaaa aagttaatac tgcacaatgc cctttacctc ttttcacctg | 180 |
| tcttcatgtc aaacctgacg tttcagagct gatgtttgca gattgggttg aatttagtcc | 240 |
| atacgaaatt ggcatggcta aatatggtac ttttatggct cccgacttat ttggaagcaa | 300 |
| attttttatg ggaacagtcg ttaagaagta tgaagaaaac cccttgcatt tcttaatggg | 360 |
| tgtctgggc agtgccttt ccatattgtt caacagagtt ttgggcgttt ctggttcaca | 420 |
| aagcagaggc tccacaatgg aggaagaatt agaaatatatt accacaaagc atattgtgag | 480 |
| taatgatagc tcggacagtg atgatgaatc acacgaaccc aaaggcactg aaaatgaaga | 540 |
| tgctggaagt gactatcaaa gtgataatca agcaagttgg attcatcgta tgataatggc | 600 |
| cttggtgagt gattcagctt tattcaatac cagagaagga cgtgctggga aggtacacaa | 660 |
| cttcatgctg gcttgaatc tcaatacatc ttatccactg tctcctttga gtgactttgc | 720 |
| cacacaggac tcctttgatg atgatgaact ggatgcagct gtagcagatc ctgatgaatt | 780 |

```
tgagcgaata tatgagcctc tggatgtcaa aagtaaaaag attcatgtag tggacagtgg    840
gctcacattt aacctgccgt atcccttgat actgagacct cagagagggg ttgatctcat    900
aatctccttt gacttttctg caaggccaag tgactctagt cctccgttca aggaacttct    960
acttgcagaa aagtgggcta aaatgaacaa gctccccttt ccaagattg atccttatgt     1020 gtttgatcgg gaagggctga aggagtgcta tgtctttaaa cccaagaatc ctgtatatgga  1080 gaaagattgc caaccatca tccactttgt tctggccaac atcaacttca gaaagtacaa    1140
ggctccaggt gttccaaggg aaactgagga agagaaagaa atcgctgact ttgatatttt    1200
tgatgaccca gaatcaccat tttcaacctt caattttcaa tatccaaatc aagcattcaa    1260
aagactacat gatcttatgc acttcaatac tctgaacaac attgatgtga taaaagaagc    1320
catggttgaa agcattgaat atagaagaca gaatccatct cgttgctctg tttcccttag    1380
taatgttgag gcaagaagat ttttcaacaa ggagtttcta agtaaaccca aagcatagtt    1440
catgtactgg aaatggcagc agtttctgat gctgaggcag tttgcaatcc catgacaact    1500
ggatttaaaa gtacagtaca gatagtcgta ctgatcatga gagactggct gatactcaaa    1560
gttgcagtta cttagctgca tgagaataat actattataa gttaggtgac aaatgatgtt    1620
gattatgtaa ggatatactt agctacattt tcagtcagta tgaacttcct gatacaaatg    1680
tagggatata tactgtattt ttaaacattt ctcaccaact ttcttatgtg tgttcttttt    1740
aaaaattttt tttcttttaa aatatttaac agttcaatct caataagacc tcgcattatg    1800
tatgaatgtt attcactgac tagatttatt cataccatga acaacacta ttttatta      1860 tatatgcata tatatacata catgaaataa atacatcaat ataaaaataa aaaaaaacgg    1920
aattc                                                               1925

<210> SEQ ID NO 4
<211> LENGTH: 2020
<212> TYPE: DNA
<213> ORGANISM: Human

<400> SEQUENCE: 4
gattattttt taaatgaaga tagttacttc catagagctt attttttgtt gttcattcag    60
gacctagtaa tttctagaag taataagact tattttttatt ataaagttat aagatttga    120 ttggaagtac tattttgaat agcattcttt ctgtgtctgt ttataaattt aaagtcatct    180
ttttctttct tctgtggaca gagaatgaat actactctga gcagtttgaa ggaaaaagtt    240
aatactgcac aatgcccttt acctcttttc acctgtcttc atgtcaaacc tgacgtttca    300
gagctgatgt ttgcagattg ggttgaattt agtccatacg aaattggcat ggctaaatat    360 ggtacttttta tggctcccga cttatttgga agcaaatttt ttatgggaac agtcgttaag    420
aagtatgaag aaaaccccttt gcatttctta atgggtgtct gggcagtgc ctttttccata    480 ttgttcaaca gagttttggg cgtttctggt tcacaaagca gaggctccac aatggaggaa    540
gaattagaaa atattaccac aaagcatatt gtgagtaatg atagctcgga cagtgatgat    600
gaatcacacg aacccaaagg cactgaaaat gaagatgctg gaagtgacta tcaaagtgat    660
aatcaagcaa gttggattca tcgtatgata atggccttgg tgagtgattc agctttattc    720
aataccagag aaggacgtgc tgggaaggta cacaacttca tgctgggctt gaatctcaat    780
acatcttatc cactgtctcc tttgagtgac tttgccacac aggactcctt tgatgatgat    840
gaactggatg cagctgtagc agatcctgat gaatttgagc gaatatatga gcctctggat    900
gtcaaaagta aaaagattca tgtagtggac agtgggctca catttaacct gccgtatccc    960
```

```
ttgatactga gacctcagag aggggttgat ctcataatct cctttgactt ttctgcaagg    1020
ccaagtgact ctagtcctcc gttcaaggaa cttctacttg cagaaaagtg ggctaaaatg    1080
aacaagctcc cctttccaaa gattgatcct tatgtgtttg atcgggaagg gctgaaggag    1140
tgctatgtct ttaaacccaa gaatcctgat atggagaaag attgcccaac catcatccac    1200
tttgttctgg ccaacatcaa cttcagaaag tacaaggctc caggtgttcc aagggaaact    1260
gaggaagaga agaaatcgc tgactttgat attttgatg acccagaatc accattttca     1320
accttcaatt ttcaatatcc aaatcaagca ttcaaaagac tacatgatct tatgcacttc    1380
aatactctga caacattga tgtgataaaa gaagccatgg ttgaaagcat tgaatataga    1440
agacagaatc catctcgttg ctctgttttcc cttagtaatg ttgaggcaag aagatttttc    1500
aacaaggagt ttctaagtaa acccaaagca tagttcatgt actggaaatg gcagcagttt    1560
ctgatgctga ggcagtttgc aatcccatga caactggatt taaaagtaca gtacagatag    1620
tcgtactgat catgagagac tggctgatac tcaaagttgc agttacttag ctgcatgaga    1680
ataatactat tataagttag gtgacaaatg atgttgatta tgtaaggata tacttagcta    1740 catttttcagt cagtatgaac ttcctgatac aaatgtaggg atatatactg tattttttaaa    1800 catttctcac caactttctt atgtgtgttc ttttttaaaaa ttttttttct tttaaaatat    1860
ttaacagttc aatctcaata agacctcgca ttatgtgatga atgttattca ctgactagat    1920
ttattcatac catgagacaa cactatttt atttatatat gcatatatat acatacatga      1980
aataaataca tcaatataaa aataaaaaaa aacggaattc                          2020
```

<210> SEQ ID NO 5
<211> LENGTH: 445
<212> TYPE: PRT
<213> ORGANISM: rat

<400> SEQUENCE: 5

```
Met Ser Thr Thr Leu Ser Ser Leu Lys Glu Lys Val Ser Ala Ala Arg
 1               5                  10                  15

Cys Pro Leu Pro Leu Phe Thr Cys Leu His Val Lys Pro Asp Val Ser
             20                  25                  30

Glu Leu Met Phe Ala Asp Trp Val Glu Phe Ser Pro Tyr Glu Ile Gly
         35                  40                  45

Met Ala Lys Tyr Gly Thr Phe Met Thr Pro Asp Leu Phe Gly Ser Lys
     50                  55                  60

Phe Phe Met Gly Thr Val Val Lys Lys Tyr Glu Glu Asn Pro Leu His
 65                  70                  75                  80

Phe Leu Met Gly Val Trp Gly Ser Ala Phe Ser Ile Leu Phe Asn Arg
                 85                  90                  95

Val Leu Gly Val Ser Gly Ser Gln Asn Lys Gly Ser Thr Met Glu Glu
            100                 105                 110

Glu Leu Glu Asn Ile Thr Ala Lys His Ile Val Ser Asn Asp Ser Ser
        115                 120                 125

Asp Ser Asp Asp Glu Ala Gln Gly Pro Lys Gly Thr Glu Asn Glu Asp
    130                 135                 140

Ala Glu Arg Glu Tyr Gln Asn Asp Asn Gln Ala Ser Trp Val His Arg
145                 150                 155                 160

Met Leu Met Ala Leu Val Ser Asp Ser Ala Leu Phe Asn Thr Arg Glu
                165                 170                 175

Gly Arg Ala Gly Lys Glu His Asn Phe Met Leu Gly Leu Asn Leu Asn
            180                 185                 190
```

```
Thr Ser Tyr Pro Leu Ser Pro Leu Arg Asp Phe Ser Pro Gln Asp Ser
            195                 200                 205
Phe Asp Asp Glu Leu Asp Ala Ala Val Ala Asp Pro Asp Glu Phe
        210                 215                 220
Glu Arg Ile Tyr Glu Pro Leu Asp Val Lys Ser Lys Ile His Val
225                 230                 235                 240
Val Asp Ser Gly Leu Thr Phe Asn Leu Pro Tyr Pro Leu Ile Leu Arg
                245                 250                 255
Pro Gln Arg Gly Val Asp Leu Ile Ile Ser Phe Asp Phe Ser Ala Arg
            260                 265                 270
Pro Ser Asp Thr Ser Pro Pro Phe Lys Glu Leu Leu Leu Ala Glu Lys
        275                 280                 285
Trp Ala Lys Met Asn Lys Leu Pro Phe Pro Lys Ile Asp Pro Tyr Val
        290                 295                 300
Phe Asp Arg Glu Gly Leu Lys Glu Cys Tyr Val Phe Lys Pro Lys Asn
305                 310                 315                 320
Pro Asp Val Glu Lys Asp Cys Pro Thr Ile Ile His Phe Val Leu Ala
                325                 330                 335
Asn Ile Asn Phe Arg Lys Tyr Lys Ala Pro Gly Val Leu Arg Glu Thr
            340                 345                 350
Lys Glu Glu Lys Glu Ile Ala Asp Phe Asp Ile Phe Asp Asp Pro Glu
        355                 360                 365
Ser Pro Phe Ser Thr Phe Asn Phe Gln Tyr Pro Asn Gln Ala Phe Lys
        370                 375                 380
Arg Leu His Asp Leu Met Tyr Phe Asn Thr Leu Asn Asn Ile Asp Val
385                 390                 395                 400
Ile Lys Asp Ala Ile Val Glu Ser Ile Glu Tyr Arg Arg Gln Asn Pro
                405                 410                 415
Ser Arg Cys Ser Val Ser Leu Ser Asn Val Glu Ala Arg Lys Phe Phe
            420                 425                 430
Asn Lys Glu Phe Leu Ser Lys Pro Thr Ala Glu Ser Ile
        435                 440                 445

<210> SEQ ID NO 6
<211> LENGTH: 1782
<212> TYPE: DNA
<213> ORGANISM: rat

<400> SEQUENCE: 6
cgatttggtt agacatatta ttttcaaatag cttttatctg tgtccatgtc tatgtattta     60
aagccacctt attcttttg tgtgtgtgtg tgaaaagaga atgagtacga ccttgagtag    120
cttgaaggaa aaggtcagcg ccgcccggtg tcctctgcct ctcttcacct gtctccatgt    180
caaaccggac gtgtcagagc tgatgtttgc cgattgggta gaatttagtc catacgaaat    240
tggcatggca aaatatggta cctttatgac tcctgacttg tttggaagca aatttttat    300 gggaacagtt gtaaaaaaat atgaagaaaa ccccttgcat ttcttaatgg gtgtctgggg    360
cagtgccttt tctatactgt tcaacagagt tttgggagtt tctggctcac agaataaagg    420
ttctacaatg gaggaggaat tagaaaatat tacagcaaag cacattgtga gtaacgacag    480
ctctgacagc gatgacgagg cccaaggacc caaaggcacc gagaatgaag atgcggaaag    540
agagtaccaa aatgacaacc aagcaagttg ggtccatcgg atgctaatgg ccttggtgag    600
tgactcagct ttattcaata cccgagaagg acgtgctggg aaggagcata acttcatgtt    660
gggcttgaat ctcaacacat cgtatccact gtctccctg agagacttca gcccccaaga    720
```

```
ttccttcgat gatgatgaac tcgacgcagc ggtagcagat ccagatgaat ttgaacgaat      780
atatgaacca ctggatgtca aaagtaaaaa gattcatgtt gtagacagtg ggctcacgtt      840
taacctgccg tatcccttga ttctgcgacc tcagagaggt gtggatctca tcatttcctt      900
tgacttttct gcaaggccaa gtgacaccag ccctccattc aaggaacttc tgcttgcaga      960
gaagtgggct aaaatgaaca agctcccttt tccaaagatt gatccttacg tgtttgatcg     1020
ggaaggattg aaggaatgct atgtgtttaa acctaagaat cctgatgtgg aaaaggattg     1080
cccaaccatt atccactttg ttctggccaa catcaacttc agaaagtaca aggcccagg      1140 tgttctgagg gaaaccaaag aagagaaaga aatagctgac tttgacattt tcgatgaccc     1200
cgaatcgcca ttttcaacct tcaacttcca gtatccaaat caagcattca aaaggctaca     1260
tgatctgatg tacttcaaca cactgaacaa cattgatgtg ataaaggatg ccattgttga     1320
gagcattgaa tacagaagac agaacccatc tcgttgctct gtttccctca gtaatgttga     1380
ggcaagaaaa ttcttcaaca aggagttcct aagtaaaccc acagcggagt ccatttgaat     1440
tccatgacta ctggagttca gagccacatg agagactcat cttactatgc acaagagact     1500
gactgctact cagagttgct ggggacggag gcgtgtgtta ggtgaaaatg gtgttgatta     1560
tgcaatactt ggcaacagtt tctgacagta tgaattttt gtacataagc atagggctat      1620
atactgtatt ttaaacattc ctcacatttt tacctgagca ttttatata tataaaaata     1680 tcctttcctt ttataaatat ttaatagtta actcagtaaa aaaaagcttc ccattgtgtg     1740
tgaatgttat tctgaactag atttgttcat gccatgttac aa                        1782

<210> SEQ ID NO 7
<211> LENGTH: 1792
<212> TYPE: DNA
<213> ORGANISM: rat

<400> SEQUENCE: 7
caattgtttt agaatacaga catctatttc cagggagctt tctttctgtt gtctaatcga       60
gaccacagat tgccagaaat aataggactt cgtttcatta taaaaagaga atgagtacga      120
ccttgagtag cttgaaggaa aaggtcagcg ccgcccggtg tcctctgcct ctcttcacct      180
gtctccatgt caaaccggac gtgtcagagc tgatgtttgc cgattgggta gaatttagtc      240
catacgaaat tggcatggca aaatatggta cctttatgac tcctgacttg tttggaagca      300 aatttttat gggaacagtt gtaaaaaaat atgaagaaaa cccttgcat ttcttaatgg        360 gtgtctgggg cagtgccttt tctatactgt tcaacagagt tttgggagtt tctggctcac      420
agaataaagg ttctacaatg gaggaggaat tagaaaatat tacagcaaag cacattgtga      480
gtaacgacag ctctgacagc gatgacgagg cccaaggacc caaaggcacc gagaatgaag      540
atgcggaaag agagtaccaa aatgacaacc aagcaagttg ggtccatcgg atgctaatgg      600
ccttggtgag tgactcagct ttattcaata cccgagaagg acgtgctggg aaggagcata      660
acttcatgtt gggcttgaat ctcaacacat cgtatccact gtctccctg agagacttca      720 gcccccaaga ttccttcgat gatgatgaac tcgacgcagc ggtagcagat ccagatgaat      780
ttgaacgaat atatgaacca ctggatgtca aaagtaaaaa gattcatgtt gtagacagtg      840
ggctcacgtt taacctgccg tatcccttga ttctgcgacc tcagagaggt gtggatctca      900
tcatttcctt tgacttttct gcaaggccaa gtgacaccag ccctccattc aaggaacttc      960
tgcttgcaga gaagtgggct aaaatgaaca agctcccttt tccaaagatt gatccttacg     1020
tgtttgatcg ggaaggattg aaggaatgct atgtgtttaa acctaagaat cctgatgtgg     1080
```

```
aaaaggattg cccaaccatt atccactttg ttctggccaa catcaacttc agaaagtaca    1140
aggccccagg tgttctgagg gaaaccaaag aagagaaaga aatagctgac tttgacattt    1200
tcgatgaccc cgaatcgcca ttttcaacct tcaacttcca gtatccaaat caagcattca    1260
aaaggctaca tgatctgatg tacttcaaca cactgaacaa cattgatgtg ataaaggatg    1320
ccattgttga gagcattgaa tacagaagac agaaccatc tcgttgctct gtttccctca    1380
gtaatgttga ggcaagaaaa ttcttcaaca aggagttcct aagtaaaccc acagcggagt    1440
ccatttgaat tccatgacta ctggagttca gagccacatg agagactcat cttactatgc    1500
acaagagact gactgctact cagagttgct ggggacggag gcgtgtgtta ggtgaaaatg    1560
gtgttgatta tgcaatactt ggcaacagtt tctgacagta tgaattttt gtacataagc    1620 ataggctat atactgtatt ttaaacattc ctcacatttt tacctgagca tttttatata    1680
tataaaaata tcctttcctt ttataaatat ttaatagtta actcagtaaa aaaaagcttc    1740
ccattgtgtg tgaatgttat tctgaactag atttgttcat gccatgttac aa           1792
```

<210> SEQ ID NO 8
<211> LENGTH: 441
<212> TYPE: PRT
<213> ORGANISM: mouse

<400> SEQUENCE: 8

```
Met Ser Met Thr Leu Ser Ser Leu Lys Glu Lys Val Asn Ala Ala Arg
 1               5                  10                  15

Cys Pro Leu Pro Leu Phe Thr Cys Leu His Val Lys Pro Asp Val Ser
             20                  25                  30

Glu Leu Met Phe Ala Asp Trp Val Glu Phe Ser Pro Tyr Glu Ile Gly
         35                  40                  45

Met Ala Lys Tyr Gly Thr Phe Met Ala Pro Asp Leu Phe Gly Ser Lys
     50                  55                  60

Phe Phe Met Gly Thr Val Val Lys Tyr Glu Glu Asn Pro Leu His
 65                  70                  75                  80

Phe Leu Met Gly Val Trp Gly Ser Ala Phe Ser Ile Leu Phe Asn Arg
             85                  90                  95

Val Leu Gly Val Ser Gly Ser Gln Asn Lys Gly Ser Thr Met Glu Glu
            100                 105                 110

Glu Leu Glu Asn Ile Thr Ala Lys His Ile Val Ser Asn Asp Ser Ser
        115                 120                 125

Asp Ser Asp Asp Glu Ala Gln Gly Pro Lys Gly Thr Glu Asn Glu Glu
    130                 135                 140

Ala Glu Lys Glu Tyr Gln Ser Asp Asn Gln Ala Ser Trp Val His Arg
145                 150                 155                 160

Met Leu Met Ala Leu Val Ser Asp Ser Ala Leu Phe Asn Thr Arg Glu
                165                 170                 175

Gly Arg Ala Gly Lys Val His Asn Phe Met Leu Gly Leu Asn Leu Asn
            180                 185                 190

Thr Ser Tyr Pro Leu Ser Pro Leu Arg Asp Phe Ser Ser Gln Asp Ser
        195                 200                 205

Phe Asp Asp Glu Leu Asp Ala Ala Val Ala Asp Pro Asp Glu Phe Glu
    210                 215                 220

Arg Ile Tyr Glu Pro Leu Asp Val Lys Ser Lys Ile His Val Val
225                 230                 235                 240

Asp Ser Gly Leu Thr Phe Asn Leu Pro Tyr Pro Leu Ile Leu Arg Pro
                245                 250                 255
```

```
Gln Arg Gly Val Asp Leu Ile Ile Ser Phe Asp Phe Ser Ala Arg Pro
            260                 265                 270
Ser Asp Thr Ser Pro Pro Phe Lys Glu Leu Leu Ala Glu Lys Trp
    275                 280                 285
Ala Lys Met Asn Lys Leu Pro Phe Pro Lys Ile Asp Pro Tyr Val Phe
    290                 295                 300
Asp Arg Glu Gly Leu Lys Glu Cys Tyr Val Phe Lys Pro Lys Asn Pro
305                 310                 315                 320
Asp Val Glu Lys Asp Cys Pro Thr Ile Ile His Phe Val Leu Ala Asn
                325                 330                 335
Ile Asn Phe Arg Lys Tyr Lys Ala Pro Gly Val Leu Arg Glu Thr Lys
                340                 345                 350
Glu Glu Lys Glu Ile Ala Asp Phe Asp Ile Phe Asp Asp Pro Glu Ser
            355                 360                 365
Pro Phe Ser Thr Phe Asn Phe Gln Tyr Pro Asn Gln Ala Phe Lys Arg
    370                 375                 380
Leu His Asp Leu Met Tyr Phe Asn Thr Leu Asn Asn Ile Asp Val Ile
385                 390                 395                 400
Lys Asp Ala Ile Val Glu Ser Ile Glu Tyr Arg Arg Gln Asn Pro Ser
                405                 410                 415
Arg Cys Ser Val Ser Leu Ser Asn Val Glu Ala Arg Lys Phe Phe Asn
                420                 425                 430
Lys Glu Phe Leu Ser Lys Pro Thr Val
            435                 440

<210> SEQ ID NO 9
<211> LENGTH: 1861
<212> TYPE: DNA
<213> ORGANISM: mouse

<400> SEQUENCE: 9
gaaaatgatt tgcttagata tgttattttg aataactttt atctgtgccc catgcctatg      60
tatttaaagc catctcttct tttcttatgt ttgtggacag aggatgagca tgaccctgag     120
tagtttgaag gaaaaggtca atgccgcccg tgtgtcctttg cctctcttca cgtgtctcca     180
cgtcaaacct gatgtgtcag agctgatgtt tgccgattgg gtggaattta gtccatatga     240
gattggcatg gcaaaatatg gtacctttat ggctcctgac ctatttggaa gcaagttttt     300
tatgggaaca gttgtaaaaa aatatgaaga aaaccccttg catttcttga tgggtgtctg     360
gggcagtgcc ttttctatac tgttcaacag agttttggga gtttctggct cacagaataa     420
aggctctaca atggaagagg aattagaaaa tattacagca aagcacatcg tgagtaatga     480
cagctccgac agtgatgatg aggctcaagg acccaaaggc accgagaatg aagaagctga     540
aaaagagtac caaagcgaca accaagcaag ttgggtccat cggatgctaa tggccttggt     600
gagcgactcg gctttattca atcccgaga aggacgtgcc ggaaaggtgc ataacttcat      660
gctgggcttg aatctcaaca catcatatcc actgtctccc ctgagagact tcagctctca     720
ggattccttc gatgacgagc tcgacgcagc ggtagcagat ccagatgaat tgaacgaat      780
atatgaacca ctggatgtca aaagtaagaa gattcatgtg gtagatagtg gctcacatt      840
taacctgcca tatcccttga ttcttcgacc tcagagaggg gtggatctta tcatctcctt     900
tgacttttct gcaaggccga gtgacaccag tccccctttc aaggaacttc tgcttgcaga     960
gaagtgggcg aaaatgaaca agcttccctt tccaaagatc gatccttatg tgtttgatcg    1020
ggaaggatta aaggaatgct atgttttaa acctaagaat cctgatgtgg agaaggattg    1080
```

```
cccaaccatt atccactttg ttctggccaa catcaacttc agaaagtaca aggccccagg    1140
tgttctaagg gaaaccaaag aagagaaaga aattgctgac tttgacattt ttgatgaccc    1200
cgaatcgcca ttttcaacct tcaactttca gtatcccaat caagcattca aaaggcttca    1260
cgatttgatg tacttcaaca cactgaacaa cattgatgtg ataaaggatg ccattgttga    1320
gagcattgaa tacagaagac agaacccatc tcgttgctct gtttccctca gtaatgttga    1380
agcaagaaaa ttcttcaata aggagtttct aagtaaaccc actgtgtaat ttctgtgctg    1440
ggatgatcaa gccatttgaa ttccatgaca atttgagttc agaagacatt agaggtcatc    1500
ttactatgca gaagagactg gctgctactc aaagttgtgg agatttagcc atgtgttagg    1560
tgaaaatgat gttgattatg taatacttag caacagtttc tgacagtatg aatttttga    1620 cattagcata gagctatata ctgtatttta acattcctc acatttttta cctgtacttt    1680
ttatataaat atgacatgtc tttttctttg aaaatattta atagtttaac tcagtaaagg    1740
agacttccca ttgtgtgtga atgttattct gaactagatt tgttcatgcc atgttacaac    1800
actattttta tttaaatgtt tatatttaca catacgaaat aaatactttg ctgtacaaat    1860
t                                                                   1861
```

<210> SEQ ID NO 10
<211> LENGTH: 1860
<212> TYPE: DNA
<213> ORGANISM: mouse

<400> SEQUENCE: 10

```
agttgtttta aaatacacac atcttttttcc ctggaacttt atttctgttg tctacttgag    60
accacagatt tccaggaata ataggacttc atttcattaa ggatgagcat gaccctgagt    120
agtttgaagg aaaaggtcaa tgccgcccgg tgtcctttgc ctctcttcac gtgtctccac    180
gtcaaacctg atgtgtcaga gctgatgttt gccgattggg tggaatttag tccatatgag    240
attggcatgg caaaatatgg tacctttatg gctcctgacc tatttggaag caagttttt    300 atgggaacag ttgtaaaaaa atatgaagaa aaccccttgc atttcttgat gggtgtctgg    360
ggcagtgcct tttctatact gttcaacaga gttttgggag tttctggctc acagaataaa    420
ggctctacaa tggaagagga attagaaaat attacagcaa agcacatcgt gagtaatgac    480
agctccgaca gtgatgatga ggctcaagga cccaaaggca ccgagaatga agaagctgaa    540
aaagagtacc aaagcgacaa ccaagcaagt tgggtccatc ggatgctaat ggccttggtg    600
agcgactcgg ctttattcaa tacccgagaa ggacgtgccg gaaaggtgca taacttcatg    660
ctgggcttga atctcaacac atcatatcca ctgtctcccc tgagagactt cagctctcag    720
gattccttcg atgacgagct cgacgcagcg gtagcagatc cagatgaatt tgaacgaata    780
tatgaaccac tggatgtcaa aagtaagaag attcatgtgg tagatagtgg gctcacattt    840
aacctgccat atcccttgat tcttcgacct cagagaggtg tggatcttat catctccttt    900
gacttttctg caaggccgag tgacaccagt ccccctttca aggaacttct gcttgcagag    960
aagtgggcga aaatgaacaa gcttcccttt ccaaagatcg atccttatgt gtttgatcgg    1020
gaaggattaa aggaatgcta tgttttttaaa cctaagaatc ctgatgtgga aaggattgc    1080 ccaaccatta tccactttgt tctggccaac atcaacttca gaaagtacaa ggccccaggt    1140
gttctaaggg aaaccaaaga agagaaagaa attgctgact ttgacatttt tgatgacccc    1200
gaatcgccat ttttcaacctt caactttcag tatcccaatc aagcattcaa aaggcttcac    1260
gatttgatgt acttcaacac actgaacaac attgatgtga taaaggatgc cattgttgag    1320
```

-continued

| | |
|---|---|
| agcattgaat acagaagaca gaacccatct cgttgctctg tttccctcag taatgttgaa | 1380 |
| gcaagaaaat tcttcaataa ggagtttcta agtaaaccca ctgtgtaatt tctgtgctgg | 1440 |
| gatgatcaag ccatttgaat tccatgacaa tttgagttca gaagacatta gaggtcatct | 1500 |
| tactatgcag aagagactgg ctgctactca aagttgtgga gatttagcca tgtgttaggt | 1560 |
| gaaaatgatg ttgattatgt aatacttagc aacagtttct gacagtatga atttttgac | 1620 |
| attagcatag agctatatac tgtattttaa acattcctca catttttac ctgtacttt | 1680 |
| tatataaata tgacatgtct tttcttttga aaatatttaa tagtttaact cagtaaagga | 1740 |
| gacttcccat tgtgtgtgaa tgttattctg aactagattt gttcatgcca tgttacaaca | 1800 |
| ctatttttat ttaaatgttt atatttacac atacgaaata aatactttgc tgtacaaatt | 1860 |

<210> SEQ ID NO 11
<211> LENGTH: 1966
<212> TYPE: DNA
<213> ORGANISM: mouse

<400> SEQUENCE: 11

| | |
|---|---|
| agttgtttta aaatacacac atcttttcc ctggaacttt atttctgttg tctacttgag | 60 |
| accacagatt tccaggaata ataggacttc atttcattat aaaatgaaaa tgatttgctt | 120 |
| agatatgtta ttttgaataa cttttatctg tgccccatgc ctatgtattt aaagccatct | 180 |
| cttcttttct tatgtttgtg gacagaggat gagcatgacc ctgagtagtt tgaaggaaaa | 240 |
| ggtcaatgcc gcccggtgtc ctttgcctct cttcacgtgt ctccacgtca aacctgatgt | 300 |
| gtcagagctg atgtttgccg attgggtgga atttagtcca tatgagattg gcatggcaaa | 360 |
| atatggtacc tttatggctc ctgacctatt tggaagcaag ttttttatgg gaacagttgt | 420 |
| aaaaaaatat gaagaaaacc ccttgcattt cttgatgggt gtctggggca gtgccttttc | 480 |
| tatactgttc aacagagttt tgggagtttc tggctcacag aataaaggct ctacaatgga | 540 |
| agaggaatta gaaaatatta cagcaaagca catcgtgagt aatgacagct ccgacagtga | 600 |
| tgatgaggct caaggaccca aaggcaccga gaatgaagaa gctgaaaaag agtaccaaag | 660 |
| cgacaaccaa gcaagttggg tccatcggat gctaatggcc ttggtgagcg actcggcttt | 720 |
| attcaatacc cgagaaggac gtgccggaaa ggtgcataac ttcatgctgg gcttgaatct | 780 |
| caacacatca tatccactgt ctccctgag agacttcagc tctcaggatt ccttcgatga | 840 |
| cgagctcgac gcagcggtag cagatccaga tgaatttgaa cgaatatatg aaccactgga | 900 |
| tgtcaaaagt aagaagattc atgtggtaga tagtgggctc acatttaacc tgccatatcc | 960 |
| cttgattctt cgacctcaga gaggtgtgga tcttatcatc tcctttgact tttctgcaag | 1020 |
| gccgagtgac accagtcccc ctttcaagga acttctgctt gcagagaagt gggcgaaaat | 1080 |
| gaacaagctt cccttttccaa agatcgatcc ttatgtgttt gatcgggaag gattaaagga | 1140 |
| atgctatgtt tttaaaccta agaatcctga tgtggagaag gattgcccaa ccattatcca | 1200 |
| ctttgttctg gccaacatca acttcagaaa gtacaaggcc ccaggtgttc taagggaaac | 1260 |
| caaagaagag aaagaaattg ctgactttga catttttgat gaccccgaat cgccattttc | 1320 |
| aaccttcaac tttcagtatc ccaatcaagc attcaaaagg cttcacgatt tgatgtactt | 1380 |
| caacacactg aacaacattg atgtgataaa ggatgccatt gttgagagca ttgaatacag | 1440 |
| aagacagaac ccatctcgtt gctctgtttc cctcagtaat gttgaagcaa gaaaattctt | 1500 |
| caataaggag tttctaagta aacccactgt gtaatttctg tgctgggatg atcaagccat | 1560 |
| ttgaattcca tgacaatttg agttcagaag acattagagg tcatcttact atgcagaaga | 1620 |

```
gactggctgc tactcaaagt tgtggagatt tagccatgtg ttaggtgaaa atgatgttga   1680
ttatgtaata cttagcaaca gtttctgaca gtatgaattt tttgacatta gcatagagct   1740
atatactgta ttttaaacat tcctcacatt ttttacctgt acttttttata taaatatgac   1800 atgtctttc ttttgaaaat atttaatagt ttaactcagt aaaggagact tcccattgtg    1860
tgtgaatgtt attctgaact agatttgttc atgccatgtt acaacactat ttttatttaa   1920
atgtttatat ttacacatac gaaataaata ctttgctgta caaatt                  1966
```

<210> SEQ ID NO 12
<211> LENGTH: 560
<212> TYPE: DNA
<213> ORGANISM: Human

<400> SEQUENCE: 12

```
taattcattt caatgatgta aagattttga atgtgtgagg aagtgctttt gtattccttt     60
tctctggaaa aaaaaaaaaa aaaaaaatt cacattttaa cccttaactg cccattccct    120
ccaagaatgg taacatttt agatgaggaa gaatgaagtt tgcctgaata gagtcaagaa    180
aggaagggga tcgcatagaa cagactcgct tgatgcatga ttgcattgat gtttcgttga   240
agataaagca gaggagcgcc tgtgacaggg agtccagggg ctaagtttct tccaggctcc   300
acagttgcta attcattctc cagttcgat gtagacatat aatctagagt tatgattatt    360
ttttaaatga agatagttac ttccatagag cttatttttt gttgttcatt caggacctag   420
taatttctag aagtaataag acttatttt attataaagt tataagattt tgattggaag    480
tactattttg aatagcattc tttctgtgtc tgtttataaa tttaaagtca tctttttctt   540
tcttctgtgg acagagaatg                                               560
```

<210> SEQ ID NO 13
<211> LENGTH: 630
<212> TYPE: DNA
<213> ORGANISM: rat

<400> SEQUENCE: 13

```
atggatagga aagtaggaaa aggaataaaa tttgaaatgt aaataaagaa atatatccaa     60 taaaaaagt aatatttagg tgagatggta agactatgca ttgcttttga gggggatgtg    120
agttcagtag tcagcaccta catctggcag cgcacaactg cctgtaactc cagctttagg   180
aggagccgat acctctggcc tttatgaaca cctacactca catgcatata tccacacaca   240
gataatatac atatgcatat tttacttttt atattcatat tttaaaataa tagaagtggt   300
agaaaaaata ctcttttgcct agtaagagtc aaataaggaa atggatcata ggaaacaaat  360
gtacttgatg tgtcaccaga gggtgacatt tcatctgaag ataaagcagg agagacggga   420
caacctgtgc cagggacacc agctgagaga attagttccc agaactatag ctgccaaatc   480
ttcccccact tcaaatgttg acacagtccc cagagattca attgttttag aatacagaca   540
tctatttcca gggagctttc tttctgttgt ctaatcgaga ccacagattg ccagaaataa   600
taggacttcg tttcattata aaaaggcaag                                    630
```

<210> SEQ ID NO 14
<211> LENGTH: 739
<212> TYPE: DNA
<213> ORGANISM: mouse
<220> FEATURE:
<221> NAME/KEY: base
<222> LOCATION: 496
<223> OTHER INFORMATION: n = a, g, c, t, unknown, or other

```
<220> FEATURE:
<221> NAME/KEY: base
<222> LOCATION: 497
<223> OTHER INFORMATION: n = a, g, c, t, unknown, or other

<400> SEQUENCE: 14
tggtaagatg gtgaatagaa gtgctattta ggtgagatcg tgaatacaag tgatattaaa      60
agcaggaagg aggaggtttt cgctcctcag cagataagcc catgcactgc tcttgtgggg     120
acatgagttc aacaaccagc acctatgtct gacagctcat aactacctgt aattccagat     180
tcaggaggtg ccaataccte tggcctctgt gaatatctgc actcacaatc atatatccac     240
acacagatac atattcatat acatatttta tttttatat tcacatttta aaataataaa      300
ttgaaatggt agaagaacac tctttgcctc ataagagaca aataaggaaa tggaccatgg     360
gaaacaaatg gacttgatgt gtcaccagag ggtgacattt catctgaaga taaagcaggg     420
gagaaaggac agctgtgcca gggaacgcca gctgagagaa ctagttctca acactctagt     480
tgccaaatct tcctcnnctt caaatgttga cacagtcttc agagattcag ttgtttttaaa    540 atacacacat cttttttccct ggaactttat ttctgttgtc tacttgagac cacagatttc    600
caggaataat aggacttcat ttcattataa aatgaaaatg atttgcttag atatgttatt     660
ttgaataact tttatctgtg ccccatgcct atgtatttaa agccatctct tctttctta     720 tgtttgtgga cagaggatg                                                  739

<210> SEQ ID NO 15
<211> LENGTH: 207
<212> TYPE: DNA
<213> ORGANISM: Human

<400> SEQUENCE: 15
ctaattcata atgtaagtta cagttcaatc tacactgctt ttataacaag tagacagaac      60
atattataat attatatttt aaataaaaga aaatgtaata cattttataa aagtcagtgg     120
actctactta tttgtccaac tatgcgtact gagcccattc tccccaccag agattataat     180
tcttctacct ttcaaactag tgcttac                                         207
```